(12) United States Patent
Wallace et al.

(10) Patent No.: US 11,617,838 B2
(45) Date of Patent: Apr. 4, 2023

(54) DRIVE MECHANISM FOR AN INJECTION DEVICE

(71) Applicant: SANOFI, Paris (FR)

(72) Inventors: Andrew Gordon Wallace, Warwick (GB); Andrew Mark Lindsay, Warwick (GB); Georgina Millington, Warwick (GB); Matthew Meredith Jones, Warwick (GB)

(73) Assignee: Sanofi, Paris (FR)

( * ) Notice: Subject to any disclaimer, the term of this patent is extended or adjusted under 35 U.S.C. 154(b) by 851 days.

(21) Appl. No.: 16/636,267

(22) PCT Filed: Feb. 15, 2018

(86) PCT No.: PCT/EP2018/053740
§ 371 (c)(1),
(2) Date: Feb. 3, 2020

(87) PCT Pub. No.: WO2018/149902
PCT Pub. Date: Aug. 23, 2018

(65) Prior Publication Data
US 2020/0246549 A1    Aug. 6, 2020

(30) Foreign Application Priority Data

Feb. 16, 2017    (EP) ..................................... 17305172

(51) Int. Cl.
*A61M 5/315*    (2006.01)
(52) U.S. Cl.
CPC ...... *A61M 5/3156* (2013.01); *A61M 5/31535* (2013.01); *A61M 5/31553* (2013.01);
(Continued)

(58) Field of Classification Search
CPC ............ A61M 5/3156; A61M 5/31535; A61M 5/31553; A61M 5/31585; A61M 2205/276; A61M 2205/8281
See application file for complete search history.

(56) References Cited

U.S. PATENT DOCUMENTS

2022/0016357 A1* 1/2022 Kohlbrenner ....... A61M 5/3204

FOREIGN PATENT DOCUMENTS

WO    WO 2012/049139        4/2012
WO    WO-2012049139 A1 *   4/2012    .............. A61M 5/24

OTHER PUBLICATIONS

International Preliminary Report on Patentability in Application No. PCT/EP2018/053740, dated Aug. 20, 2019, 7 pages.
(Continued)

*Primary Examiner* — Nathan R Price
*Assistant Examiner* — Anh Bui
(74) *Attorney, Agent, or Firm* — Fish & Richardson P.C.

(57) ABSTRACT

The disclosure relates to an injection device for expelling of a number of preset or user-selectable doses of a medicament. The injection device includes an elongated housing extending along an axial direction and configured to accommodate a cartridge containing the medicament and having a bung sealing a proximal end of the cartridge, a windup expelling mechanism, and a dose setting mechanism. The dose setting mechanism includes a handle, a dose tracking member, and a limiter. The dose tracking member is rotatable relative to the housing within a range of positional states and operatively connectable to the handle for tracking a rotation thereof. The limiter is operationally engageable with the dose tracking member and a trigger of the windup expelling mechanism for blocking actuation of the trigger when the dose tracking member is in one of a number of predetermined sections of the range of positional states.

20 Claims, 11 Drawing Sheets

(52) U.S. Cl.
CPC ... *A61M 5/31585* (2013.01); *A61M 2205/276* (2013.01); *A61M 2205/8281* (2013.01)

(56) References Cited

OTHER PUBLICATIONS

International Search Report and Written opinion in Application No. PCT/EP2018/053740, dated May 22, 2018, 9 pages.

\* cited by examiner

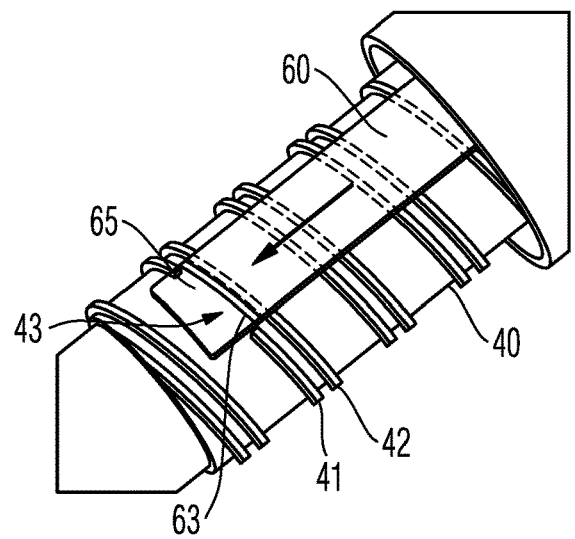
Fig. 7
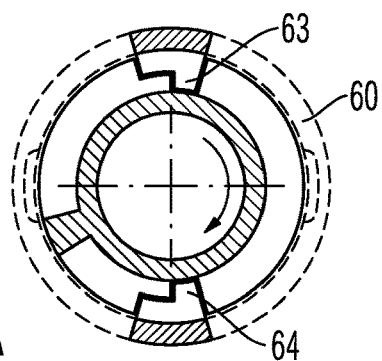
Fig. 8 A-A
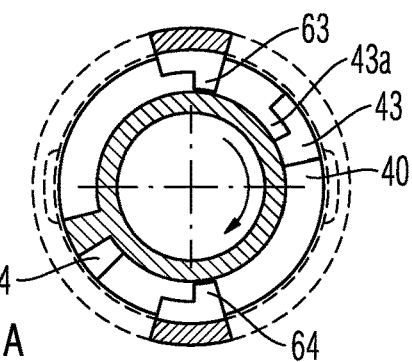
Fig. 9 A-A
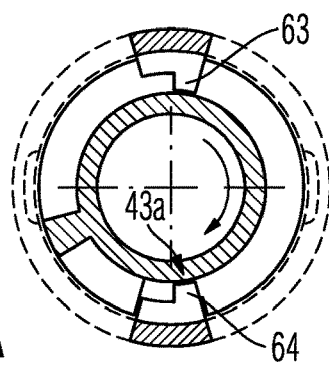
Fig. 10 A-A

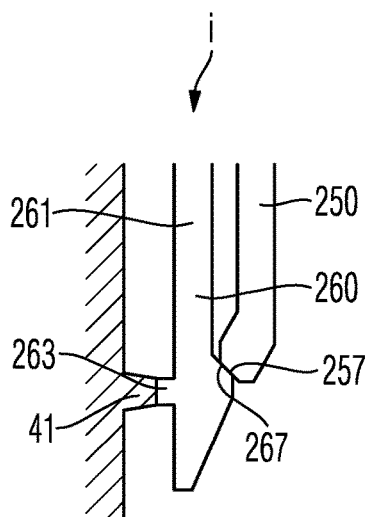
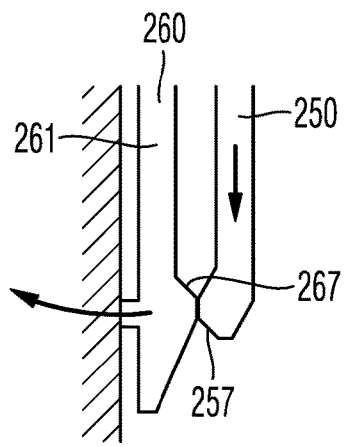
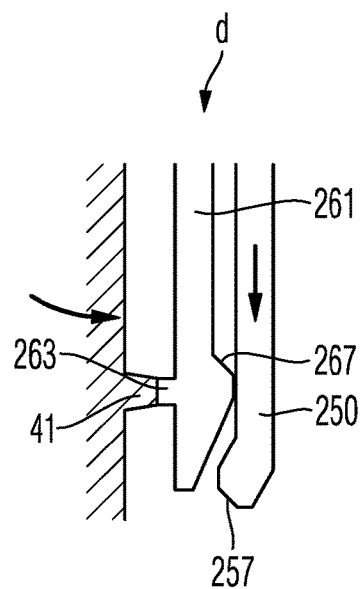
Fig. 18                Fig. 19                Fig. 20
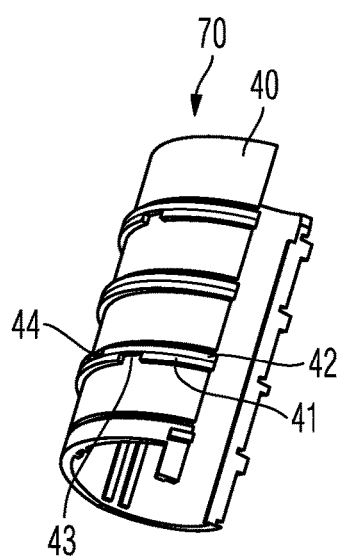
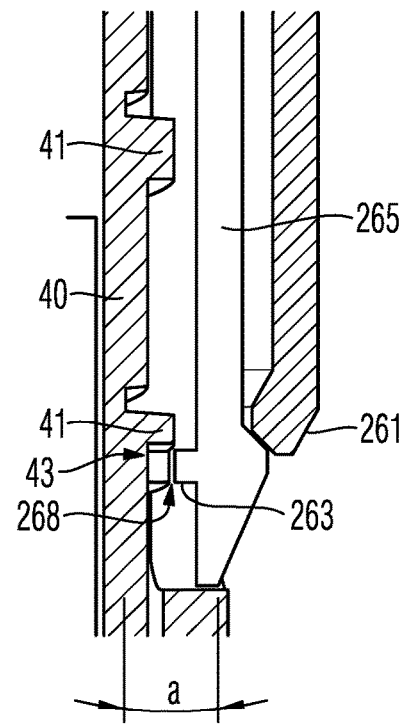
Fig. 21                Fig. 22

DRIVE MECHANISM FOR AN INJECTION DEVICE

CROSS-REFERENCE TO RELATED APPLICATIONS

The present application is the national stage entry of International Patent Application No. PCT/EP2018/053740, filed on Feb. 15, 2018, and claims priority to Application No. EP 17305172.3, filed on Feb. 16, 2017, the disclosures of which are incorporated herein by reference.

TECHNICAL FIELD

The disclosure relates to one aspect of an injection device, such like a pen-type injector for expelling of preset or user-selectable doses of a medicament. In particular, the disclosure relates to an injection device comprising a windup expelling mechanism and comprising a dose setting mechanism, wherein the dose setting mechanism is configured to impede or to block a dose expelling procedure when the dose actually set does not match a predefined or prescribed dose size.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism or expelling mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential doses of a medication may be required. For example the range of doses may be needed to satisfy the therapeutic needs of different user groups, or to allow individual users to deliver a different dose at different times of the day e.g. in the morning or in the evening.

It is therefore desirable to have an injection device that provides a limitation of deliverable dose values to a limited number of generally available dose values. The injection device should allow delivery of only one or several fixed dose values. The injection device should be configured to prevent setting or expelling of doses that do not match with a pre-described or predefined dose size.

SUMMARY

In one aspect an injection device is provided for expelling of a number of preset or user-selectable doses of a medicament, the injection device comprises:
  an elongated housing extending along an axial direction (z) and configured to accommodate a cartridge containing the medicament and having a bung sealing a proximal end of the cartridge,
  a windup expelling mechanism comprising a piston rod, a mechanical energy reservoir and a trigger, wherein the trigger is movable between an idle position (i) and a dose expelling position (d) relative to the housing and configured to, when moved into the dose expelling position (d), release energy from the mechanical energy reservoir to the piston rod thereby axially driving the piston rod relative to the housing in order to urge against the bung,
  a dose setting mechanism comprising a handle for rotationally selecting a dose and/or for arming the windup expelling mechanism, a dose tracking member and a limiter, wherein the dose tracking member is rotatable relative to the housing within a range of positional states and operatively connectable to the handle for tracking a rotation thereof, and wherein the limiter is operationally engageable with the dose tracking member and the trigger for blocking actuation of the trigger when the dose tracking member is in one of a number of predetermined sections of the range of positional states.

The windup expelling mechanism provides mechanical energy to drive and to move the piston rod in a distal axial direction, i.e. towards a dispensing end of the injection device. By means of the trigger mechanical energy stored in the mechanical energy reservoir is releasable. By means of one or several clutches the mechanical energy is transferable into a driving momentum or driving force acting on the piston rod for driving the same in distal direction relative to the housing. The trigger may be operably connected to one or several clutches of the windup expelling mechanism and/or of the dose setting mechanism in order to release a distally directed motion of the piston rod under the effect of a depleting mechanical energy reservoir.

The dose tracking member is typically located inside the housing. It is rotatable relative to the housing. It may comprise a cylindrical geometry and may be completely arranged inside the housing. The dose tracking member may be selectively engageable with the handle, typically at least during dose setting, i.e. when the injection device is in a dose setting mode. The dose tracking member may be axially fixed to the housing. Alternatively, the dose tracking member may be rotationally and translationally coupled to the housing. The dose tracking member and the housing may be threadedly engaged. A position or orientation of the dose tracking member relative to the housing is directly correlated to the size of a dose actually set. Typically, the dose tracking member is displaceable between a zero dose configuration, in which the size of the dose set by the dose setting mechanism equals zero and a maximum dose configuration, in which the size of the dose set by the dose setting mechanism is at a maximum.

The dose tracking member is continuously displaceable relative to the housing. The magnitude of a displacement of the dose tracking member in comparison to the zero dose configuration is directly proportional to the size of the dose actually set. Any variation of the orientation or position of the dose tracking member relative to the housing is correlated to a respective variation of the size of a dose actually set.

The limiter is operationally engageable with the dose tracking member for blocking actuation of the trigger. The trigger may be selectively or permanently operationally engaged with the limiter. The trigger and the limiter may be arrangeable in an abutment configuration. The abutment configuration may coincide with the idle position (i) or with the dose expelling position (d). The abutment configuration may be also located there between. When in the abutment configuration the trigger may be axially engaged with the limiter. A further axial displacement of the trigger, e.g. in a distal direction, and beyond the abutment configuration is only possible when the limiter is allowed to move relative to the dose tracking member.

A longitudinal or axial movement or translational displacement of the limiter relative to the dose tracking member is blocked when the dose tracking member is in one of a number of predetermined sections of the range of possible positional states. The respective movement is only allowed if the dose tracking member is located outside the number of predetermined sections of the range of possible positional states. In the present context the term "positional states" refers to the position and/or the orientation of the dose tracking member. If the dose tracking member is outside the predetermined sections of the range of possible positional states the mutual interaction of the dose tracking member and the limiter is such that the limiter is hindered to be displaced or to be moved relative to the dose tracking member. In this way and due to an abutment configuration between the limiter and the trigger a further displacement of the trigger towards the dose expelling position is effectively blocked and impeded.

In this case an actuation force acting on the trigger and being large enough to displace the trigger from the idle position towards and into the dose expelling position is counteracted by the abutment of the trigger with the limiter and further through the engagement of the limiter with the dose tracking member. Typically, the dose tracking member is axially fixed in a selected positional state. The limiter may be in axial abutment with the dose tracking member at least towards a distally directed displacement relative to the dose tracking member. Furthermore the trigger may be in axial abutment with the limiter. In this way a distally directed dispensing force acting on the trigger is counteracted by the axial engagement of the housing with the dose tracking member, the axial engagement of the dose tracking member with the limiter and the axial engagement of the limiter with the trigger. In effect and when in a blocking configuration, the interaction of the dose tracking member with the limiter and with the trigger impedes an actuation of the trigger towards the dose expelling position. Consequently, a dispensing action or an expelling procedure cannot be triggered or initiated.

In one example the operational engagement between the dose tracking member and the limiter comprises a first pair of keying features and a second pair of keying features that are located on the limiter and on the dose tracking member.

One pair of keying features comprises at least a first keying feature and a second keying feature. The first keying feature is located on the dose tracking member and the second keying feature is located on the limiter the first keying feature and the second keying feature constitute a pair of keying features. The first and the second keying features of a pair of keying features comprise complementary shapes and mutually corresponding geometries. The first keying feature and the second keying feature are configured such that a displacement or movement of the limiter relative to the dose tracking member is only possible when the first keying feature matches and aligns with the second keying feature of a pair of keying features. In all other positional states in which the first and the second keying features do not match or in which the first and second keying features are not properly aligned a movement of the limiter relative to the dose tracking member, typically a distally and axially directed movement of the limiter relative to the dose tracking member, is effectively impeded.

There is provided also a second pair of keying features also having a first keying feature and a second keying feature, wherein the first keying feature is located on the dose tracking member and wherein the second keying feature is located on the limiter. Likewise the first pair of keying features also the keying features of the second pair of keying features comprise complementary shapes and mutually corresponding geometries. The first keying feature and the second keying feature of the second pair of keying features are also configured such that a displacement or movement of the limiter relative to the dose tracking member is only possible when the first keying feature matches and aligns with the second keying feature of the second pair of keying features.

To achieve a blocking of the trigger and/or of the limiter it is generally sufficient when the keying features of only one pair of the first and second pair of keying features mutually engage.

In one embodiment the keying features of the first pair of keying features and the keying features of the second pair of keying features are configured such that the first pair of keying features and the second pair of keying features simultaneously engage or simultaneously disengage. Hence, when the keying features of the first pair of keying features are engaged so as to block or to impede actuation of the trigger or displacement of the limiter also the keying features of the second pair of keying features will be engaged. In this way, the first pair of keying features and the second pair of keying features simultaneously provide a multiple abutment configuration or blocking configuration. Any forces or counterforces between the limiter and the dose tracking member can be distributed among the first pair of keying features and the second pair of keying features. In effect, maximum forces or a force effect present to individual keying features of the first or second pair of keying features can be reduced in this way. This allows and supports a miniaturized and intricate design of the keying features because a maximum force effect or a maximum load that may be applied via the trigger and the limiter is distributed among the plurality of available keying features.

The injection device is not generally limited to only a first pair of keying features and a second pair of keying features. There may be provided also a third pair of keying features or even more pairs of keying features.

In another example the dose tracking member is engaged with the housing by a slotted link arranged along a cylindrical surface, and wherein the movement of the dose tracking member includes a rotation around a long axis (z) of the cylindrical surface.

The slotted link may provide a combined translational and rotational displacement of the dose tracking member relative to the housing. The slotted link may comprise a helical shape. The slotted link may be formed between an outside facing sidewall portion of the dose tracking member and an inside facing sidewall portion of the housing. The dose tracking member may comprise a cylindrical shape and the housing may comprise a cylindrical shape. An outer diameter of the dose tracking member may be smaller than an inner diameter of the housing. The dose tracking member may be completely accommodated inside the housing. The cylindrical surface of the slotted link may be provided on the outside of the dose tracking member and/or on the inside of the housing. Typically, the slotted link is provided on the inside of the housing, which is cylindrically shaped. The dose tracking member may also comprise a cylindrical structure. It may comprise a shell structure or an annular structure to fit into the housing. The long axis of the cylindrical surface may coincide with a longitudinal axis of the elongated housing.

In another example the operational engagement between the dose tracking member and the limiter comprises one or more elongated keying structures, wherein each of the keying structures being arranged in parallel or being formed integrally with the slotted link between the dose tracking member and the housing.

The elongated keying structure on the dose tracking member is configured to define those positional states of the dose tracking member in which expelling of a dose of the medicament is allowable and supported. There may be provided at least one elongated keying structure between the dose tracking member and the limiter. The elongated keying structure may be provided on an outside facing sidewall portion of the dose tracking member. It may be also provided on an inside of the dose tracking member. The elongated keying structure may be characterized by at least one keying feature. The keying feature may comprise an interruption of the elongated keying structure or may comprise a recess in the elongated keying structure.

When having two or more elongated keying structures for instance on the dose tracking member each of the two or more elongated keying structures extends parallel to the other of the elongated keying structures of the dose tracking member. In a similar manner the elongated keying structures may be also provided on the limiter. Typically, one of the dose tracking member and the limiter comprises an elongated keying structure to operationally engage with a keying feature of the other one of the dose tracking member and the limiter.

The keying structure of one of the dose tracking member and the limiter and a keying feature of the other one of the dose tracking member and the limiter may form or may constitute at least one of the pair of keying features.

The elongated keying structures may be integrally formed with the slotted link that is provided between the dose tracking member and the housing. In one embodiment the elongated keying structure comprises a helically wound thread on an outside facing sidewall portion of the dose tracking member. The helically wound thread may comprise a double function. A portion thereof may be in threaded engagement with a correspondingly shaped threaded section on an inside facing sidewall portion of the housing. Another portion thereof may form or may contribute to the pair of keying features between the dose tracking member and the limiter. When implemented on or with the dose tracking member the elongated keying structures provide a well-defined threaded engagement between the dose tracking member and the housing. They further provide at least two keying features of two pairs of keying features to engage with the limiter.

In another example the rotation of the dose tracking member includes a translation along the axis (z) of the cylindrical surface. The slotted link may be configured as a helically wound thread between the dose tracking member and the housing. Correspondingly and in accordance with the pitch of the thread, a rotation of the dose tracking member relative to the housing always comes along with a longitudinal movement or translation thereof along the long axis of the cylindrical surface, hence along the axial direction as defined by the elongated housing.

In another example the slotted link comprises a continuously wound thread. The continuously wound thread may be provided on one of the dose tracking member and the housing. If the continuously wound slotted link is provided on an inside facing sidewall portion of the housing it is sufficient when the dose tracking member comprises a threaded section on an outside facing sidewall portion that may be intersected or interrupted. In an alternative the continuously wound thread may be provided on an outside facing sidewall portion of the dose tracking member. It would then be sufficient when the inside facing sidewall portion of the housing only comprises a threaded section of limited size.

Having a continuously wound thread on the inside facing sidewall portion of the housing enables to implement and interrupted or recessed threaded section on the outside facing sidewall portion of the dose tracking member. Recesses or interruptions in the threaded section of the dose tracking member may provide a keying feature to engage with a correspondingly shaped keying feature of the limiter.

In another example the limiter is arranged for actuation coaxially with the axis (z) of the cylindrical surface. The limiter may be rotationally fixed or rotationally secured to the housing. It may be axially displaceable relative to the housing between a blocking position (b) and a release position (r). The blocking position may coincide with a proximal end position. The release position may coincide with a distal end position of the limiter. If the dose tracking member is an allowable positional state the keying features of the dose tracking member and the limiter mutually match and the limiter is movable from the proximal locking position towards the distal release position. In other, hence, non-allowable positional states of the dose tracking member the limiter is effectively hindered or impeded to be moved from the proximal blocking position towards the distal release position. Since the limiter may be in axial abutment with the trigger a respective axial displacement of the trigger is blocked or impeded accordingly.

In another example the handle is operatively connectable to the mechanical energy reservoir for harvesting energy from rotational actuation of the handle and for arming the mechanical energy reservoir.

The handle may provide a double function. In one aspect it may provide setting of a user selectable dose. In another aspect it may be configured for arming the windup expelling mechanism. Setting of a dose by actuating or moving the handle relative to the housing in a dose incrementing fashion may increase the energy level stored by the mechanical energy reservoir. The handle may be selectively connectable to the mechanical energy reservoir at least during dose setting, i.e. when the dose setting mechanism and/or the windup expelling mechanism is in a dose setting mode. When operably connected or coupled to the mechanical energy reservoir actuation or movement of the handle may act against a restoring force provided by the mechanical energy reservoir. The mechanical energy reservoir may be configured as a spring or may comprise a spring, e.g. a torsion spring or a helically wound spring.

In another example the limiter is axially connected to the trigger for transferring axial-translational forces from the limiter to the trigger.

The limiter may be permanently fixed to the trigger and vice versa so that any movement or axial translation of the trigger equally transfers into a corresponding movement or axial translation of the limiter. In another example the trigger may be axially displaceable relative to the housing against the action of a trigger spring. In the idle position the trigger may be separated from the limiter. It may be only due to and during an axially directed movement or displacement of the trigger that the trigger gets in axial abutment with the limiter. The trigger may then be in an abutment configuration with the limiter. In the abutment configuration the trigger may be located axially between the idle position and the dose expelling position. A further axial displacement of the trigger towards the expelling position may then slave the limiter and may displace the limiter accordingly in axial direction, e.g. in axial distal direction. The limiter and the trigger may comprise mutually corresponding fastening elements by way of which the limiter is displaceable from the release position towards the blocking position. A proximally directed displacement of the limiter from the release position towards the initial blocking position may be conducted by the trigger and by the trigger spring.

In another example the trigger is axially displaceable relative to the housing, wherein the limiter is axially engageable with the trigger and wherein the limiter has a first engaging section and a second engaging section, wherein the first engaging section is circumferentially offset from the second engaging section.

In another example the at least one keying feature of the first pair of keying features is located on the first engaging section and wherein at least one keying feature of the second pair of keying features is located on the second engaging section. The keying features of the two pairs of keying features that are located on the limiter may be exclusively located and provided on the first and the second engaging sections of the limiter, respectively. Since the first and second engaging sections are tangentially or circumferentially offset they are mechanically engaged with keying features of the first and second pair of keying features that are located on the dose tracking member. The keying features on the dose tracking member will be arranged at a corresponding circumferential offset. When the first pair of keying features and the second pair of keying features simultaneously engage in a blocking configuration the circumferential offset of the first pair of keying features and of the second pair of keying features effectively prevents a tilting or canting of the limiter relative to the dose tracking member and relative to the housing. By means of at least two pairs of keying features that are arranged at a circumferential offset any axially directed force effect provided to the trigger and to the limiter accordingly can be counteracted in a more balanced way.

In another example at least one of the first engaging section and the second engaging section is configured to engage with one of the elongated keying structures on the dose tracking member to impede movement of the trigger towards the dose expelling position (d). Typically, the keying features provided on the first and on the second engaging sections engage with the correspondingly shaped elongated keying structures on the dose tracking member. The keying features and the keying structures are configured such that they simultaneously engage or simultaneously disengage in order to provide an at least twofold blocking in cases where the positional states of the dose tracking member corresponds to a non-allowed dose size.

In another example the one or more elongated keying structures comprise at least one of a first outer thread and a second outer thread on an outside surface of the dose tracking member.

As an example, there may be provided a first outer thread and a second outer thread on the outside surface of the dose tracking member. At least one of the first and second outer threads may be threadedly engaged with the slotted link or with an inner threaded section of the housing. At least one of the first and second outer threads may provide a keying feature of at least one of the first and second pairs of keying features to engage with a correspondingly shaped keying feature on at least one of the first and second engaging sections.

The first and the second outer thread may be arranged intertwined. The first and the second outer thread may be arranged in a nested configuration, hence in an axially overlapping configuration. In some examples, the first and the second outer thread are completely axially separated. There, one of the first and second outer threads may be provided at a distal section of the dose tracking member whereas another one of the first and second outer threads may be provided at a proximal portion of the dose tracking member. The distal portion and the proximal portion of the dose tracking member may be non-overlapping.

With another example the keying features of at least one of the first engaging section and the second engaging section comprise a radially inwardly extending protrusion. Typically, at least one of the first engaging section and the second engaging sections is configured to engage with at least one of the first outer thread and the second outer thread.

It is conceivable that the first engaging section and the second engaging section both comprise at least one radially inwardly extending protrusion, wherein at least one of the protrusions is engaged with at least one of the first outer thread and the second outer thread. Typically, the first and the second protrusions may be in engagement with the first and with the second outer thread, respectively. When having a first and a second radially inwardly extending protrusion the first and the second engaging sections can be located radially outside the dose tracking member. The axial extension of the protrusions is smaller than the axial distance between two neighboring threaded structures of the first and the second outer thread. In this way the protrusions can be permanently engaged with the first and the second outer thread.

In another example the first outer thread and the second outer thread have the same thread pitch and wherein the first engaging section is engageable with the first outer thread and wherein the second engaging section is engageable with the second outer thread. Typically, the first protrusion is engaged with the first thread. Simultaneously, the second protrusion is engaged with the second thread. First and second protrusions are typically arranged circumferentially offset. They may be hence arranged at a predefined tangential distance from each other. When arranged circumferentially offset and when simultaneously engaged with the first outer thread and the second outer thread the first and the second engaging sections provide a distribution of mechanical load that is present on the limiter. A tilting or canting of the limiter relative to the dose tracking member can be prevented in this way. Moreover, the mechanical engagement and the reliability of an axial force transfer from the trigger to the limiter and further to the dose tracking member can be improved. Since the first and the second outer thread comprise an identical thread pitch the first and the second protrusions remain in a threaded or mechanical engagement with the first and with the second thread, respectively, even when the dose tracking member is subject to a rotational movement relative to the limiter.

In another example the second outer thread is located at a predefined axial offset from the first outer thread and wherein the axial offset is larger than or equal to an axial distance between the idle position and the dose dispensing position of the trigger. By arranging the first and the second outer thread at a predefined axial offset the first and the second outer thread may be individually encoded. For instance, the first and the second outer thread may be provided with at least one or several recesses that allow and support an axial movement of keying features of the limiter axially through and beyond the respective thread. A predefined axial distance between the first outer thread and a second outer thread enables at least a limited axial displacement of the limiter relative to the dose tracking member when the keying features of the dose tracking member are aligned with the keying features of the limiter. This limited axial displacement may be sufficient to switch the dose setting mechanism and/or the windup expelling mechanism from the dose setting mode into the dose dispensing mode and hence to support and to enable a triggering of a dose expelling procedure.

The keying features of the dose tracking member and the limiter may be configured such that the first pair of keying features and the second pair of keying features simultaneously align so as to enable an axial displacement of the limiter relative to the dose tracking member. Otherwise and if one pair of keying features is out of alignment also the other pair of keying features will be out of alignment. In such a configuration the keying features of the limiter will be in engagement with the keying structures of the dose tracking member. For instance, the protrusions of the first and the second engaging section are in mechanical engagement and hence in axial abutment with the first and the second outer thread of the dose tracking member.

In another example the second outer thread is located at a predefined radial offset from the first outer thread. Instead of an axial separation of first and second outer thread it is even conceivable that the first and the second outer thread axially overlap. Here, the first outer thread may comprise a first radially outwardly extending dimension and the second outer thread may comprise a second radially outwardly extending dimension. The second dimension may be larger than the first dimension. Accordingly, correspondingly shaped first and second protrusions of the first and second engaging sections may comprise differently sized radially inwardly extending dimensions. When the first protrusion is configured to engage with the first outer thread and when the second protrusion is configured to engage with the second outer thread the radially inwardly directed extension of the second protrusion may be shorter than the radially inwardly directed extension of the first protrusion. In this way, the first and second thread may be individually encoded or may be provided individually with recesses through which the first and the second protrusions may pass through in the axial direction, respectively.

In another example the at least one of the first outer thread and the second outer thread is discontinuous and comprises at least a first recess, wherein the first recess is shaped to receive the protrusion and/or wherein the protrusion is axially displaceable through the first recess. The tangential or circumferential extension of the first recess is at least as large as a corresponding tangential or circumferential extension of the at least one protrusion of the first engaging section or second engaging section. In this way the at least one protrusion can axially slide through the recess. The at least one protrusion may axially pass by or may pass through the respective outer recess.

Typically, the first outer thread and the second outer thread each comprise at least a first recess configured to receive the first protrusion and to receive the second protrusion of the first engaging section and the second engaging section, respectively. If the dose tracking member is in an allowable positional state, i.e in a state in which a dose dispensing or dose expelling action is allowed and supported by the injection device, the first protrusion will be aligned with a recess of the first outer thread and the second protrusion will be aligned with a recess in the second outer thread. In this configuration the limiter is axially displaceable relative to the dose tracking member. The first protrusion may slide through the at least one recess of the first outer thread and the second protrusion may simultaneously pass through the at least one recess of the second outer thread.

Typically, the at least one recess of the first outer thread and the at least one recess of the second outer thread are arranged at a predefined circumferential offset. The circumferential offset between the recess of the first outer thread and the at least one recess of the second outer thread is substantially identical to the circumferential of said of the first keying feature and the second keying feature of the limiter. In other words the circumferential offset between the recesses is identical or corresponds to the circumferential offset of the first protrusion and the second protrusion that are provided on the first engaging section and the second engaging section of the limiter.

In another example the slotted link comprises an inner threaded section on the housing and comprises at least one of the first outer thread and the second outer thread on the dose tracking member. Here, at least one of the first outer thread and the second outer thread fulfills a double function. The respective outer thread is not only configured to provide an axial abutment for the limiter but also serves to provide a threaded engagement between the dose tracking member and the housing of the injection device. With some examples, the inner threaded section on the inside facing sidewall of the housing is located axially offset and at a predefined axial distance from the keying features of the limiter. The housing may therefore comprise an axially extending slot or recess on an inside facing sidewall to slidably support the limiter. The slot or recess can be located at a predefined axial distance from the inner threaded section. In this way there can be provided sufficient space for an axially slidable displacement of the limiter inside the housing.

In another example:
the inner threaded section is located axially adjacent to at least one of the first engaging section and the second engaging section, or
the inner threaded section axially overlaps with at least one of the first engaging section and the second engaging section, wherein the inner threaded section is arranged tangentially adjacent to at least one of the first engaging section and the second engaging section of the limiter.

With this example the inner threaded section comprises a circumferential or tangential extension that is shorter than 180° or shorter than 120° or shorter than 80° of the total circumference of the housing, which is typically cylindrically shaped and comprises a circular cross-section. There may be provided two or more inner threaded sections on an inside facing sidewall of the housing to engage with at least one of the first and the second outer thread. It is conceivable to have a first inner threaded section located circumferentially between the first and the second engaging sections of the limiter and to have a second inner threaded section located circumferentially between the first and the second engaging sections of the limiter.

The first and the second threaded sections may be threadedly engaged with the first outer thread of the dose tracking member. Alternatively, they may be threadedly engaged with the second outer thread of the dose tracking member. It is also conceivable that the first inner threaded section is threadedly engaged with the first outer thread and that the second inner threaded section is threadedly engaged with the second outer thread. A multiple threaded engagement of the dose tracking member and the housing provides a reliable and secure arrangement of the dose tracking member inside the housing that is substantially free of backlash, canting or tilting.

Moreover, with an axially overlapping configuration of the first engaging section and the threaded engaging section with the inner threaded section the total axial elongation of the injection device can be reduced. In effect a compact design of the injection device can be provided.

In another example the limiter comprises a proximal end section to engage with the trigger and wherein the limiter is axially displaceable relative to the housing between a proximal blocking position and a distal release position. Typically, the limiter is axially slidably displaceable relative to the housing. Hence, the trigger is transferable from the proximal blocking position to the distal release position by way of a sliding motion relative to the housing. Typically, the limiter is located inside the housing. It is displaceable from the blocking position towards the release position by means of the trigger.

The limiter may comprise an annular shape at a proximal end section. By means of an annular shaped proximal end forces transferred from the trigger towards and into the limiter in the distal direction may be received and can be evenly distributed among the first and the second engaging sections of the dose tracking member. The proximal end of the limiter may be shaped to correspond to a shape of a distal end of the trigger. Both, the trigger and the limiter may have an annular abutment section so as to evenly transfer any distally directed force effect from the trigger towards the limiter. In this way any tilting motion or cant of the limiter can be effectively prevented.

In another example the limiter comprises a first axially extending leg and a second axially extending leg, wherein the first leg comprises or forms the first engaging section and wherein the second leg comprises or forms the second engaging section. The first leg and the second leg may extend parallel with respect to each other. They may be arranged at diametrically opposite locations on the outer circumference of the dose tracking member. It is conceivable that the limiter comprises three or more legs extending parallel in the axial direction from a proximal end section of the limiter towards the distal direction.

The keying features of the limiter may be provided at a distal end section of the legs. Hence, radially inwardly extending protrusions of the keying features may be provided at a free end of the first and the second legs, respectively. In radial direction the legs may be sandwiched between an inside facing portion of the sidewall and the outer circumference of the dose tracking member. The radial thickness of the legs is dimensioned so as to fit between an inside facing sidewall portion of the housing and the at least first or second outer thread on the dose tracking member. In this way a radial deformation or radial movement of the keying features of the dose tracking member can be effectively limited. The keying features of the limiter may therefore remain in permanent mechanical engagement with the keying structure on the outer circumference of the dose tracking member.

In another example the first leg and the second leg are resiliently deflectable in a radial direction and wherein the first leg and the second leg each comprise a radially and axially extending beveled section at a radially outwardly facing side to engage with a complementary shaped counterpart section of the trigger. With this example the mutually corresponding keying features of the limiter and the dose tracking member are configured for a radial displacement. If the dose tracking member is in an allowable positional state in which dose dispensing or dose expelling is supported the keying features of the limiter may be radially displaceable relative to the dose tracking member.

For this, the dose tracking member may comprise radially extending recesses on its outer circumference. The radially extending recesses may be also provided in at least one of the first and the second outer threads. A radially inwardly directed deflection of the keying features of the limiter is only allowed and possible if the keying features of the limiter are correctly aligned with correspondingly shaped keying features of the dose tracking member. Then and in response to an axially directed displacement of the trigger the engaging sections of the limiter will be subject to a radially inwardly directed displacement. In this way, the engaging sections of the limiter will give way to the trigger and may support and allow a distally directed displacement of the trigger relative to the limiter.

Otherwise and if the dose tracking member is in a non-supported or non-allowed positional state, the keying features of the limiter and the dose tracking member are out of alignment and a radially inwardly directed displacement of the keying features of the limiter is effectively prevented, e.g. by a radial abutment of the keying features of the limiter by the keying structure of the dose tracking member. It is then that the beveled section of the limiter is and remains in axial abutment with the complementary shaped beveled section of the trigger. If the beveled section of the limiter is hindered to deflect radially inwardly by means of the radial abutment between the respective engaging section or leg of the limiter with an outer circumference or keying structure of the dose tracking member a distally directed displacement of the trigger is effectively blocked.

In another example a radially inwardly directed deflection of at least one of the first leg and the second leg in response to a distally directed displacement of the trigger is impeded as long as at least one protrusion of the first leg and the second leg is engaged with at least one of the first thread and the second thread. A radially inwardly directed deflection of at least one of the first and the second legs is supported and allowed as soon as the respective keying feature of the limiter is aligned with the corresponding keying feature of the dose tracking member.

Typically, the first and the second keying features of the limiter simultaneously align with correspondingly shaped keying features of the dose tracking member. The beveled section of the first leg and of the second leg of the first and the second engaging sections of the limiter are both in abutment or engagement with the correspondingly shaped beveled section of the trigger. A distally directed depression of the trigger from the idle position towards the dose dispensing position then leads to a radially inward deflection or movement of the engaging section and hence of the legs of the limiter. Due to this radially inwardly directed movement or deflection the trigger can be displaced from the idle position towards the dose expelling position and the process of dose expelling can be triggered.

In another example there is further provided a number sleeve comprising a helical shaped sequence of dose indicating numbers on its outer circumference and wherein the dose tracking member is configured as the number sleeve or wherein the dose tracking member comprises a threaded tracking sleeve rotationally locked and axially displaceably engaged with the number sleeve. By configuring the dose tracking member as the number sleeve the total number of components of the dose setting mechanism or of the windup expelling mechanism can be reduced. This enables a further miniaturization of the injection device. Moreover, costs for production and assembly of the injection device can be reduced in this way.

When implemented as a number sleeve and when having a first and a second outer thread the pitch of the first and the second outer threads may be sufficiently large so that consecutive numbers are arranged along a helical structure extending between adjacent convolutions of the first and the second outer thread. As seen in an axial direction the first thread may be followed by the second thread. The threads may be separated at a predefined axial offset "O". Then there may follow a display portion that is provided with dose indicating numbers. Further in axial direction there will follow the next convolution of the first thread. In some configurations the axial extension or the axial height of the display portion is larger than the axial offset between the first and the second outer thread. This implies a comparatively large thread pitch of the first and the second outer thread. In some configurations the axial extension of the display portion is at least twice as large as the axial offset between the first and the second outer thread.

In another example the keying features of the limiter comprise a an angled or beveled edge complementary shaped to a chamfered end section of at least one of the keying structures of the dose tracking member and wherein the limiter is axially displaceable towards a blocking position through engagement with the chamfered end section. With this example the limiter may be moved axially as a result of a rotational motion of the dose tracking member. In an initial configuration the keying features of the limiter may be arranged in an at least partially overlapping configuration with the chamfered section of the keying structures of the dose tracking member.

When the dose tracking member is subject to a rotation, e.g. during a dose setting procedure the beveled edge of the keying features may engage and may slide along the chamfered end section of the at least one keying structure of the dose tracking member. Consequently, the keying feature of the limiter and hence the entire limiter may become subject to an axial displacement towards and into a a blocking position as the dose tracking member is rotated and as long as the dose tracking member is in one of a number of predetermined sections of the range of positional states, in which a dose dispensing or dose expelling action is effectively blocked.

The axial displacement of the limiter may then lead to a blocking of the trigger. Here, it is conceivable that a proximal end section of the limiter engages at least one blocking member that is e.g. pivotable or movable relative to the housing. The axial displacement of the limiter may lead to a movement or pivoting motion of the blocking member. When arriving in a blocking position the blocking member may effectively prevent a depression or actuation of the trigger.

With this example it may be of particular benefit that any force effect applied to the trigger is only and exclusively transferred to the blocking member, which may be pivotably or movably connected to the housing. In this way any counterforces to prevent actuation of the trigger are provided or supported by the housing. The dose tracking member and the limiter are located outside a flux of force or outside of a load path.

In another example the mechanical energy reservoir comprises a helical driving spring having a first end connected to the housing and having a second end connected to the dose tracking member and wherein the dose tracking member is rotatable in a dose incrementing direction against the action of the driving spring. The helical driving spring may serve and provide the mechanical energy reservoir. Since the helical driving spring is connected with oppositely located ends to the dose tracking member and to the housing, respectively the helical driving spring may be tensed or biased during dose setting, i.e. when the dose tracking member is subject to a rotation relative to the housing in a dose incrementing direction. In this way mechanical energy stored in the helical driving spring is increased during the dose setting procedure. During a dose dispensing procedure the previously stored mechanical energy can be released from the helical driving spring. The dose tracking member may then be subject to a rotation in a dose decrementing direction. The helical driving spring may be pretensed. In an initial configuration, i.e. in the zero dose configuration the helical spring may be preloaded with a predefined amount of mechanical energy. In this way it is guaranteed that the mechanical energy stored in the helical driving spring is sufficient to conduct a dose dispensing procedure and to drive the piston rod in a distal direction during the dose dispensing or dose expelling procedure.

In another example there is further provided a driver axially displaceable between a dose setting position and a dose dispensing position and wherein the handle is rotatable relative to the housing for setting of a dose of the medicament, wherein when in the dose dispensing position the driver is rotationally locked to the piston rod and is rotationally disengaged from the handle and wherein when in the dose setting position, the driver is rotationally disengaged from the piston rod and is rotationally locked to the handle.

The driver may be implemented as a drive sleeve. The driver may be permanently rotationally connected to the dose tracking member. The mechanical energy reservoir, e.g. the helical driving spring may be connected with its second end to the driver. In the dose expelling or dose dispensing mode the driver will the released to rotate in the dose decrementing direction under the action of the driving spring. Typically, there is provided at least a first clutch between the handle and the driver. There may be provided a second clutch between the driver and the piston rod. In the dose setting mode the first clutch is closed so that a rotation of the handle equally transfers to a rotation of the driver while the second clutch is open. In this way the driver can be rotated relative to the housing and relative to the piston rod. In the dose setting mode the piston rod is stationary relative to the housing.

For switching the dose setting mechanism and/or the windup expelling mechanism from the dose setting mode into the dose dispensing or dose expelling mode the first clutch is opened while the second clutch is closed. Typically, the second clutch is closed and the driver is rotationally locked to the piston rod before the first clutch is opened or released. In this way it is guaranteed that mechanical energy stored in the mechanical energy reservoir does not dissipate in an uncontrolled way. In the dose dispensing mode the driver is rotated in the dose decrementing direction under the action of the mechanical energy reservoir. At the same time the dose tracking member returns into its initial or zero dose position. Numbers of a number sleeve typically appearing in a window of the housing successively decrease during the dose dispensing or dose expelling procedure. At the same time the handle is disconnected from the driver and does not rotate.

In another example there is provided a cartridge filled with the medicament and arranged inside the housing. The cartridge typically comprises a tubular—shaped or cylindrical barrel. Near a distal or dispensing end the barrel comprises a narrowing shoulder portion. The distal end of the cartridge may comprise a pierceable seal, such as a septum. The pierceable seal is penetrable by a double-tipped injection needle. The injection needle is typically releasably connectable to a dispensing end of the housing of the injection device. The housing of the injection device may comprise a proximal housing component also denoted as main housing component. The housing may further comprise a distal housing component also denoted as cartridge holder. The cartridge is typically accommodated in the cartridge holder. The windup expelling mechanism and the dose setting mechanism are typically accommodated in the main housing component. With disposable injection devices the main housing component and the cartridge holder are unreleasably connected. With reusable injection devices the main housing component and the cartridge holder are detachably or releasably connected so as to enable a replacement of an empty cartridge.

In the present context a distal end or distal direction refers to that end section of the injection device from which the liquid medicament is expelled. The proximal end or proximal direction refers to that end section of the injection device which is furthest away from biological tissue of a patient to be treated with the medicament. The injection device is typically configured for administration of a liquid medicament, such as insulin or heparin. The injection device is typically configured for self-medication. It is configured for operation by only one hand of a user. The trigger typically provided at the proximal end of the injection device is configured to be depressed by a thumb of a user while residual fingers of the same hand may grip the housing of the injection device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention as it is defined by the claims. Further, it is to be noted, that any reference numerals used in the appended claims are not to be construed as limiting the scope of the invention.

BRIEF DESCRIPTION OF THE FIGURES

In the following various embodiments of a data collection device in connection with an injection device are described by making reference to the drawings, in which:

FIG. 7 shows a perspective view of the arrangement of FIG. 6, FIG. 8 is a cross-section A-A according to FIG. 5 with the dose tracking member in an allowable positional state, FIG. 9 is a cross-section according to FIG. 8 with the dose tracking member rotated by about 75° compared to the configuration of FIG. 8, FIG. 10 shows a further cross-section according to FIG. 8 with the dose tracking member rotated by about 180° compared to the configuration of FIG. 8, FIG. 18 shows a detailed and enlarged view of the distal end of the limiter and the trigger in the configuration of FIG. 16, FIG. 19 shows the configuration according to FIG. 18 with the trigger slightly displaced in distal direction and FIG. 20 shows the distal end of the trigger and the limiter in the configuration according to FIG. 17, FIG. 21 is a partially cut and perspective view of the dose tracking member according to FIGS. 16 to 20, FIG. 22 is an enlarged view of the limiter in engagement with the dose tracking member according to FIG. 21.

DETAILED DESCRIPTION

Figure 1:
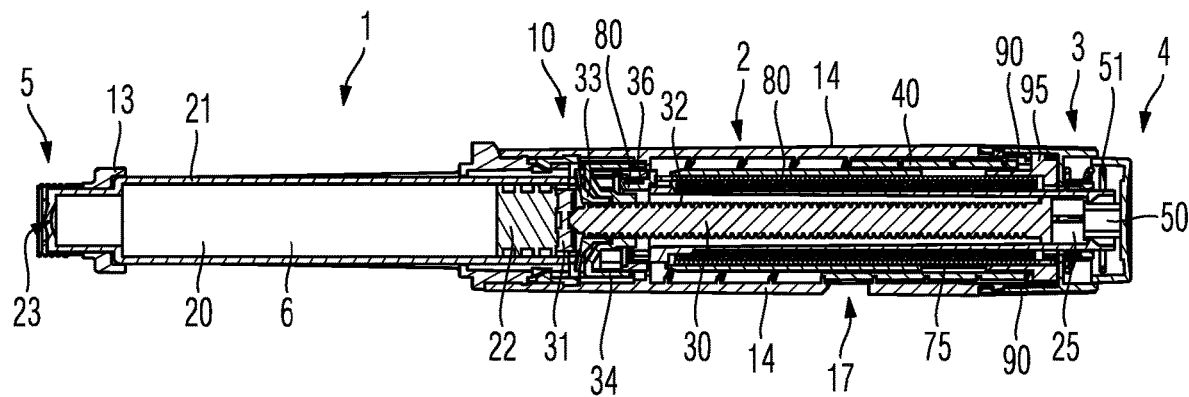
FIG. 1 shows an longitudinal cross-section through an example of a hand held injection device.
Figure 2:
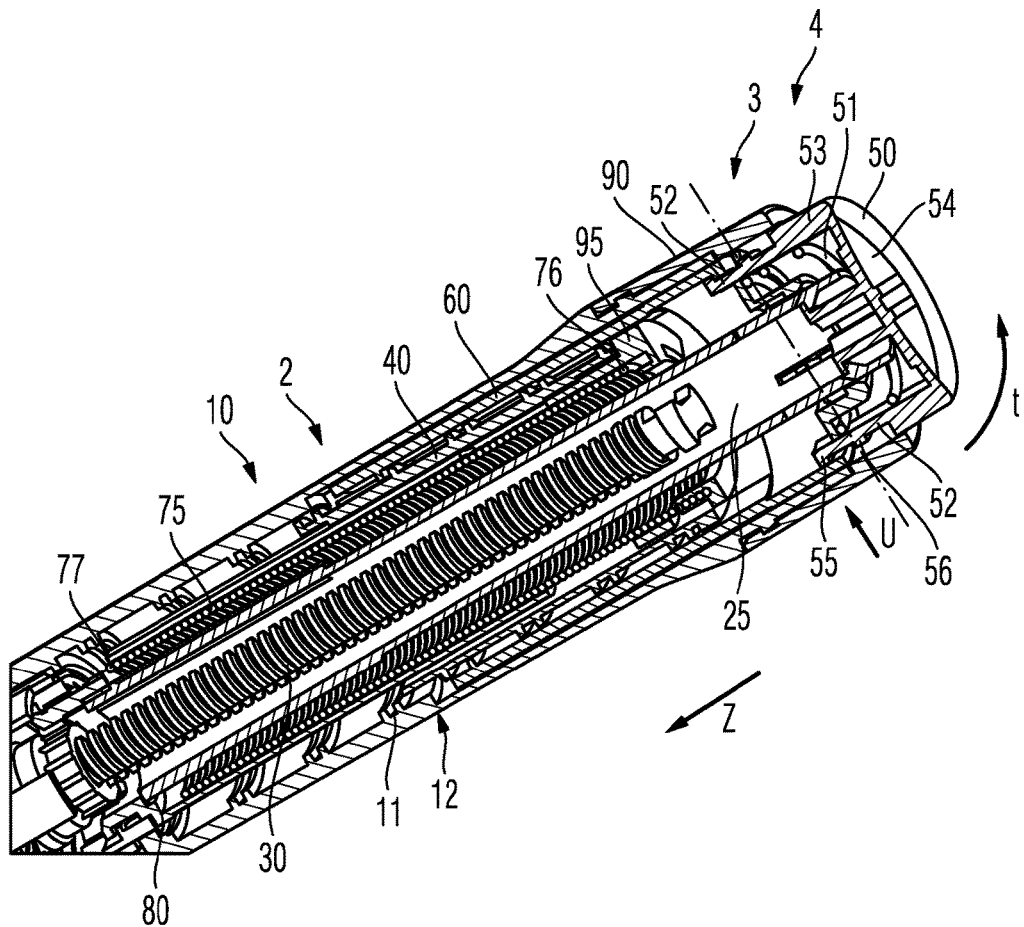
FIG. 2 is a perspective view of the proximal end of the injection device of FIG. 1.

The injection device 1 as shown in FIGS. 1 and 2 comprises a housing 10 of elongated shape. The injection device 1 is configured as a handheld injection device. The housing 10 is of substantially tubular shape. It extends from a proximal end 4 to a distal end 5. The housing 10 comprises a cartridge holder 13 forming a distal end of the housing 10 and further comprises a main housing component 14 forming a proximal end of the housing 10. The cartridge holder 13 is configured to accommodate a cartridge 20. The cartridge 20 comprises a barrel 21 filled with a liquid medicament 6. Near its proximal end the barrel 21 is sealed with a bung 22 that is displaceably arranged inside the barrel 21 for expelling of the liquid medicament 6 through the distal end of the cartridge 20. Typically, the distal end of the cartridge 20 is sealed by a pierceable seal 23. The distal end of the cartridge 20 is typically located near and inside the distal end of the cartridge holder 13. The distal end of the cartridge holder 13 comprises an outer threaded section to releasably engage with a correspondingly shaped threaded section of a needle hub (not illustrated).

The fastening of the needle hub to the distal end of the cartridge holder 13 comes along with a penetration of the pierceable seal 23. In this way the double-tipped injection needle gains access to the interior of the cartridge 20. The injection needle is hence in fluid communication with the medicament 6 inside the cartridge. By exerting a distally directed pressure onto the bung 22 the medicament 6 can be expelled through the injection needle from the interior of the cartridge 20 and into biological tissue.

A distally directed advancing motion of the bung 22 is provided by a piston rod 30 of a windup expelling mechanism 2 that is located inside the housing 10, in particular inside the main housing component 14. The injection device 1 further comprises a dose setting mechanism 3. The dose setting mechanism 3 is also located and accommodated inside the housing 10, in particular inside the main housing component 14. The windup expelling mechanism 2 and the dose setting mechanism 3 comprises numerous mechanically interacting components. There may be provided some components of the injection device 1 that belong to both, the dose setting mechanism 3 and to the windup expelling mechanism 2.

The specific implementation of an exemplary injection device will be described later on. Typically, the dose setting mechanism provides an individual dialing or setting of a dose of variable size. For this the user may grab a handle 90 provided near the proximal end 4 of the injection device 1. Setting of a dose may be conducted by rotating the handle 90 in a clockwise or counterclockwise direction, i.e. in a dose incrementing direction. For dispensing of the dose of the medicament the user has to depress the trigger 50 at the proximal end 4 of the injection device thereby initiating a dose expelling or dose dispensing procedure.

The windup expelling mechanism 2 has a mechanical energy reservoir 75. The mechanical energy reservoir 75 may comprise a helically shaped drive spring. During dose setting the mechanical energy reservoir 75 may be armed or biased. A driving motion or a driving momentum applied to the handle 90 may serve to increase the energy level stored in the mechanical energy reservoir 75. During dose dispensing and when depressing the trigger 50 at least a portion of the previously stored mechanical energy is released. Consequently, the mechanical energy provided by the mechanical energy reservoir 75 is transferred into a distally directed driving motion of the piston rod 34 thereby urging the bung 22 towards the distal end 5.

The injection device 1 and the dose setting mechanism 3 are configured to provide setting and dispensing of doses of the medicament 6 of variable size. The user himself may determine the amount of medicament to be injected in a dose expelling procedure. A user may for instance select a dose between 0 units and 120 units of a medicament, e.g. a respective amount of international units (IU) of insulin. The injection device 1 as described herein provides a limitation of generally available dose sizes to a number of predetermined dose sizes. The dose setting mechanism and the windup expelling mechanism are configured to block or to prevent dispensing of a dose of a medicament having an inappropriate size. In this way the injection device can is limited and configured to enable a dose dispensing action only when the previously set dose is within a range of allowable doses to be set and dispensed.

For all other dose sizes the dose setting mechanism and/or the windup expelling mechanism is blocked. In this way and when a user sets or dials a dose of the medicament of an inappropriate size, e.g. a dose being too large or a dose being too small for a specific therapeutic treatment the dose actually set cannot be dispensed.

In order to achieve this blocking functionality depression of the trigger 50 at or near the proximal end 4 of the injection device 1 is effectively blocked.

Figure 3:
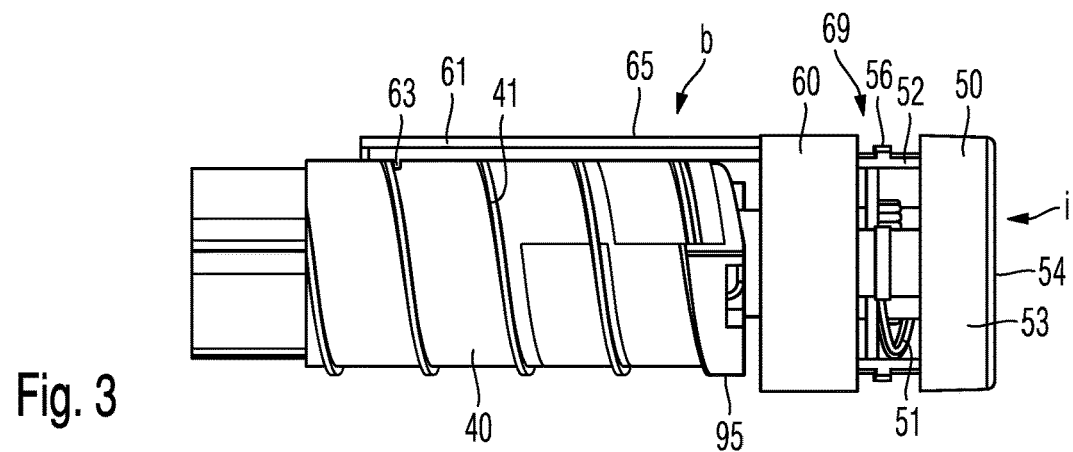
FIG. 3 is a side view of the dose tracking member, the limiter and the trigger in an initial configuration.

One embodiment of such a blocking function is now described in FIGS. 3 to 10. In this example the injection device 1 comprises a dose tracking member 40, a limiter 60 and a trigger 50. The dose tracking member 40 is movably arranged inside the housing 10, in particular inside the proximal or main housing component 14. The dose tracking member 40 is rotatable relative to the housing 10 within a range of positional states. As it is apparent from a comparison of FIGS. 3, 4 and 5, the dose tracking member 40 can be displaced in a longitudinal direction of the injection device 1. In FIG. 3, the dose tracking member 40 is in an initial configuration that may correspond to a zero-dose configuration and hence to a configuration of the dose setting mechanism 3 where the dose actually set equals 0.

By setting of a dose and e.g. when rotating the handle 90 in a dose incrementing direction, e.g. clockwise as seen in FIG. 2, the dose tracking member 40 will be subject to a distally directed motion. At least during dose setting the dose tracking member 40 is rotationally coupled or rotationally locked to the handle 90. A rotation of the handle 90 in a clockwise direction directly leads to a corresponding rotation of the dose tracking member 40. In the present example the dose tracking member 40 is engaged with the housing 10 by a slotted link 12. For instance, the slotted link 12 comprises two mutually corresponding threaded structures on the inside facing sidewall portion of the proximal housing component 14 and on the outer circumference of the dose tracking member 40.

The slotted link 12 may be formed by a threaded section 11 on the inside facing sidewall of the main housing component 14 and by a keying structure 41 on the outer circumference of the dose tracking member 40. The keying structure 41 may comprise a helical thread protruding radially outwardly from a cylindrically shaped outer surface of the dose tracking member 40.

The dose tracking member 40 may comprise a sleeve-shaped geometry. It may be substantially cylindrically-shaped.

Due to the slotted link 12 between the dose tracking member 40 and the housing 10 the dose tracking member 40 is subject to a combined rotational and axial motion as the handle 90 is turned relative to the housing 10. As the dose tracking member 40 is turned or as the dose tracking member 40 is rotated relative to the housing 10 it assumes different positional states. Hence, the axial position as well as a degree of rotation gradually changes as the dose tracking member 40 is rotated relative to the housing 10. Any positional states, i.e. any axial position as well as any rotational position of the dose tracking member relative to the housing 10 is characteristic and unique for a dose of a specific size.

The limiter 60 is rotationally fixed to the housing 10. It is axially, e.g. axially slidable displaceable relative to the housing 10 within a limited range. The limiter 60 is operationally engageable with the dose tracking member 40 for blocking actuation of the trigger 50 when the dose tracking member 40 is in one of a number of predetermined sections of the range of positional states. In other words, if a non-allowed dose size has been set and if the dose tracking member 40 is hence located in a respective positional state the dose tracking member is operably engaged with the limiter 60 so as to prevent a distally directed displacement of the limiter 50. In this way and since the limiter 60 is also axially engageable with the trigger 50, the trigger 50 cannot be displaced towards the distal end 5. The trigger 50 is axially locked or blocked and is hence hindered to be displaced in a dose dispensing position d as indicated in FIG. 5.

Figure 4:
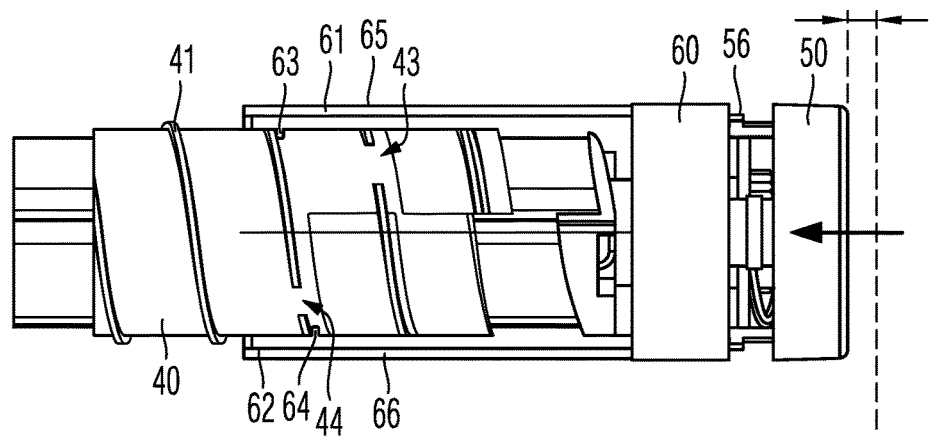
FIG. 4 is another side view of the arrangement according to FIG. 3 after a dose of a predetermined size has been set.

The operational engagement between the dose tracking member 40 and the limiter 60 comprises a first pair of keying features and a second pair of keying features that are located on the limiter 60 and on the dose tracking member 40, respectively. In FIG. 4 the limiter 60 comprises two keying features, namely a first keying feature 63 and a second keying feature 64. The first and second keying features 63 and 64 are located and are separated at a circumferential offset relative to each other. The first keying feature 63 and the second keying feature 64 both comprise a radially inwardly extending protrusion to engage with a correspondingly shaped keying structure 41 on the outside of the dose tracking member 40. As it is apparent from FIG. 4, the first and second keying features 63, 64 of the limiter 60 are in axial abutment with the radially outwardly protruding keying structure 41 of the dose tracking member 40. In this way and as long as distally facing edge of face of the keying features 63, 64 is in axial abutment with a proximal side edge of the keying structure 41 the limiter 60 is hindered to be displaced in longitudinal direction, in particular towards the distal end 4 of the injection device 1.

As indicated in FIG. 4, the keying structure 41 of the dose tracking member 40 comprises a first keying feature 43 and a second keying feature 44. Here, the keying features 43, 44 comprise a recess or an interruption in the keying structure 41. In circumferential direction the keying features 43, 44 are at least as large as the extension of the first and the second keying features 63, 64 of the limiter 60. In a particular positional state of the dose tracking member 40 that correspond to an allowable size of a dose to be dispensed the keying features 43, 44 of the dose tracking member 40 are aligned axially or axially inline with the correspondingly shaped keying features 63, 64 of the limiter 60.

Figure 5:
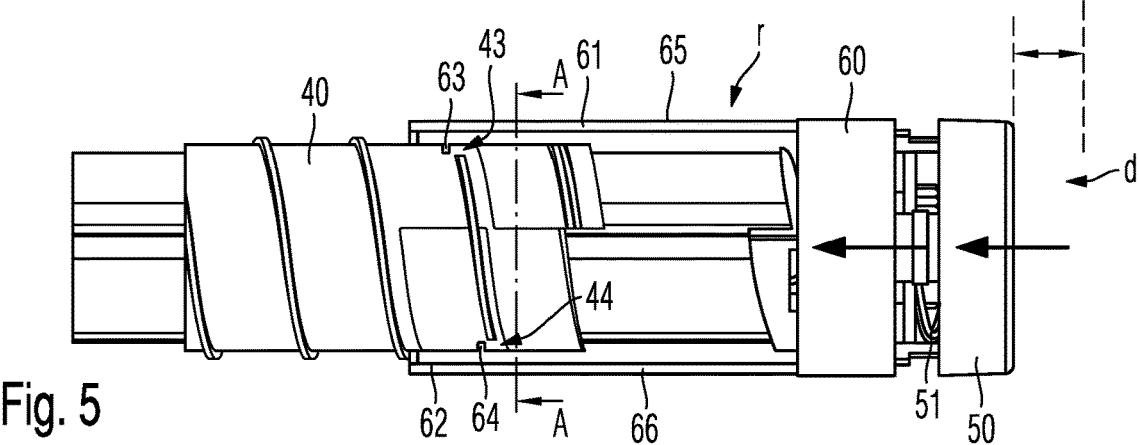
FIG. 5 shows a further configuration of the arrangement of FIGS. 3 and 4 with the trigger and the limiter being depressed in distal direction.

Then, as shown in FIG. 5, the limiter 60 can be displaced in distal direction when depressing the trigger 50 accordingly. When subject to a distally directed displacement the keying feature 63 of the limiter 60 is axially displaced through the keying feature 43 on the dose tracking member 40, and hence through the recess or gap formed by the keying feature 43. Likewise and simultaneously also the keying feature 64 will slide through the correspondingly shaped keying feature 44 of the dose tracking member 40.

Figure 6:
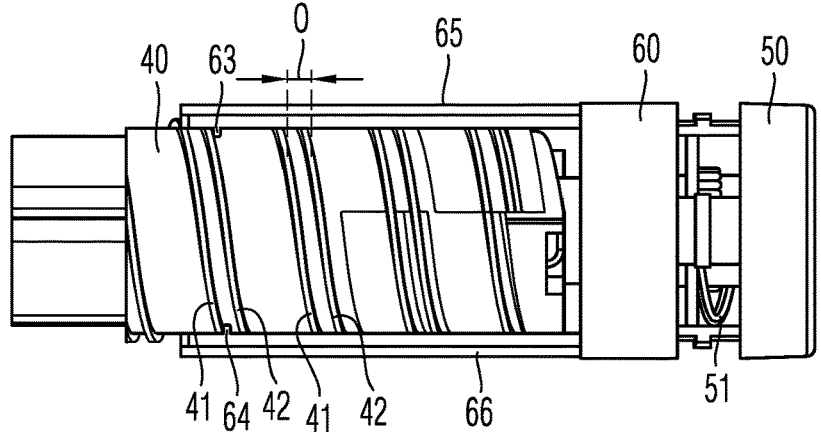
FIG. 6 shows another example of a dose tracking member in an arrangement according to FIGS. 2 to 5.

Once the keying features 63, 64 of the limiter 60 have traveled past and through the correspondingly shaped keying features 43, 44 of the dose tracking member 40 the dispensing procedure can be triggered. During the dose dispensing procedure the dose tracking member 40 will be subject to a reverse motion until it returns and arrives in the initial zero-dose position as shown in FIG. 3. When reaching the zero dose configuration the keying features 63, 64 of the limiter 60 will be aligned with correspondingly shaped zero-dose keying features of the dose tracking member 40 that allow a proximally directed movement of the limiter 60 relative to the dose tracking member 40. Then and at the end of a dose dispensing procedure the user may release the trigger 50, which under the effect of a trigger spring 51 will return into its idle position i as shown in FIGS. 3 and 6.

The trigger 50 comprises a circular or cylindrically-shaped button portion 53 with a closed proximal end face 54. The button portion 53 comprises a cylindrically-shaped sidewall from which numerous strut portion 52 extend axially and towards the distal end 5. The strut portions 52 each comprise a first radial protrusion 55 and a second radial protrusion 56 as shown in FIGS. 2 and 3. The radial protrusion 55, 56 may each comprise a radially outwardly extending rib. The first radial protrusion 55 is located at a distal end of the strut portion 52 and protrudes radially outwardly. The first radial protrusion 55 is engaged and connected to a correspondingly shaped radially inwardly extending rim or protrusion 68 of the limiter 60. A proximal end face of the first protrusion 55 is in axial abutment with a distally facing end face of the protrusion 68 on the inside sidewall of the proximal end section 69 of the limiter 60. In this way and when urged in proximal direction by the trigger spring 51 the trigger 50 drags the limiter 60 back into its initial position as shown in FIG. 3.

The second radial protrusion 56 protruding radially outwardly from the axially extending strut portion 52 is located proximally from the proximal end of the limiter 60. The second radial protrusion 56 may comprise a radial extension that is larger than an inner diameter of the proximal end section 69 of the limiter 60. In this way and when depressing the trigger 50 in distal direction the second radial protrusion 56 axially abuts with a proximal end face 67 of the limiter 60. The proximal end face 67 may be provided on an annular shaped proximal end section 69 of the limiter 60. The first and second keying features 63, 64 are located distally from the proximal end section 69. They are provided on first and second engaging sections 61, 63 extending axially and distally from the proximal end section 69. Typically and as shown in FIGS. 2 to 10 the keying features 63, 64 are provided at an inside facing portion of a first leg 65 forming the first engaging section 61 and a second leg 66 forming the second engaging section 62. The engaging section 61, 62 and hence the legs 65, 66 have a limited circumferential dimension or extension as shown in FIG. 7. The engaging section 61, 62 or the legs 65, 66 may comprise a circumferential extension of the less than 45°, less than 30°, less than 20° or less than 15°. A limited circumferential dimension of the engaging sections 61, 62 or of the respective legs 65, 66 is beneficial to reduce a package size of the device. The dose tracking member 40 can be threadedly engaged with the housing 10 by means of at least one of the keying structures 41, 42. A threaded portion of the housing 10 threadedly engaged with at least one of the keying structures 41, 42 of the dose tracking member 40 may be located and arranged axially overlapping with the engaging sections 61, 62 or may be arranged axially overlapping with legs 65, 66 of the limiter 60.

Alternatively, the limiter 60 may also comprise a cylindrical structure with a closed circumferential side wall, wherein the first and the second engaging sections 61, 62 are integrated into the sidewall of the limiter 60. Here, the engaging sections 61, 62 may each comprise a protrusion extending radially inwardly from an inside surface of the cylindrical sidewall of the limiter 60. With a cylindrically-shaped limiter 68 threaded engagement of the dose tracking member 40 with the housing 10 may be located axially offset from the limiter 60.

The first engaging section 61 comprises the first keying feature 63 and the second engaging section 62 comprises the second keying features 64. As it is shown in FIGS. 4 to 6 the first and second keying features 63, 64 of the limiter 60 are arranged diametrically opposite around the outer circumference of the dose tracking member 40. The offset of the first and the second keying features 63, 64 may be in a range of 180°. In this way and when in a blocking configuration and hence in a blocking position b as indicated in FIG. 4 the first and the second keying feature 63, 64 of the limiter 60 are in simultaneous axial abutment with at least one of the keying structures 41 of the dose tracking member 40.

Typically, the first and the second keying features 63, 64 are in axial abutment with the first and with the second keying structures 41, 42 and in particular with first and second keying features 43, 44 of the dose tracking member 40.

In this way and when exerting a distally directed force to the trigger 50 the limiter 60 will experience a corresponding force effect in a distal direction through the engagement of the strut portion 52 with the proximal end section 69 of the limiter 60. Since the first and the second keying features 63, 64 are both in axial abutment with the keying structure 41 on the outside circumference of the dose tracking member 40, the axial force effect acting on the trigger 50 and hence on the limiter 60 distributes among the first and the second keying features 63, 64 and among the first and second engaging sections 61, 62.

The axial load on the dose tracking member 40 is balanced in this way. Having a first and a second keying feature 63, 64 that are spaced apart from each other in the circumferential direction prevents and counteracts any tilting motion or cant of the limiter 60 relative to the dose tracking member 40. In addition, axial load transferred from the limiter 60 to the dose tracking member 40 is introduced rather symmetrically and homogeneously into the dose tracking member 40. In this way also a tilting motion or cant of the dose tracking member 40 inside the housing 10 can be reduced or can be entirely eliminated.

Typically, there are provided two pairs of keying features on the dose tracking member 40 and on the limiter 60. The dose tracking member 40 and the limiter 60 are both configured such that a first pair of keying features and a second pair of keying features simultaneously engage or simultaneously disengage. When the first keying feature 63 of the limiter 60 axially aligns with a first keying feature 43 on the dose tracking member 40 also the second keying feature 64 of the limiter 60 axially aligns with the second keying feature 44 of the dose tracking member 40. It is then that each pair of keying features, namely a first pair of the keying features 43, 63 and a second pair of keying features 44, 64 both allow or prevent axial displacement of the limiter 60 relative to the dose tracking member 40 in distal direction.

For setting of a dose the dose tracking member 40 may be subject to a rotation larger than 120° or larger than 180°. Moreover, the dose tracking member 40 may be subject to more than one or more than two entire revolutions with the longitudinal axis as an axis of rotation. In order to have a unique and distinct encoding on the dose tracking member 40 it is conceivable that the geometry of the keying features 63, 64 of the limiter 60 are different so that only a first keying features 63 of the limiter 60 is configured to align and to pass through a first keying feature 43 of the dose tracking member 40 and that a second keying feature 64 of the limiter 60 does not match with the first keying feature 43 of the dose tracking member 40. The second keying features 64 of the limiter 60 may only match and may only properly align with the second keying feature 44 of the dose tracking member 40. If the first and the second keying features of the dose tracking member 40 and of the limiter 60 should be equidistantly spaced apart in circumferential direction, e.g. if two keying features should be separated by about 180° or if three keying features should be separated by about 120° there will be only one distinct and unique positional state of the dose tracking member 40 at which the keying features of the dose tracking member 40 and the limiter 60 properly align.

Such a situation is shown in FIGS. 8 through 10. There, the keying features 63, 64 of the limiter 60 are mirror symmetric but not rotationally symmetric. Hence, the keying feature 63 and the keying features 64 are of substantially identical shape. The keying feature 63 as shown on top of FIG. 8 may be transferred into the keying feature 64 near the bottom of FIG. 8 by way of a reflective projection with regards to a horizontal line extending through the center of the limiter 60. As it is apparent from FIG. 9 the dose tracking member 40 comprises a first and a second keying feature 43, 44 each of which having a geometric shape that matches with only one of the geometric shapes of the keying features 63, 64 of the limiter 60. Only in one positional state of the dose tracking member 40 as shown in FIG. 8 the first keying feature 63 of the limiter 60 matches and axially aligns with the first keying feature 43 of the dose tracking member 40. Simultaneously, also the second keying feature 64 axially aligns with the second keying feature 44 of the dose tracking member 40. As the dose tracking member 40 is rotated by e.g. 180°, as shown in FIG. 10, the keying feature 64 of the limiter 60 remains in axial engagement with a section 43a of the keying feature 43 of the dose tracking member 40.

In the example as shown in FIGS. 8 through 10 the mutually corresponding keying features 43, 44, 63, 64 comprise an L-shaped geometry and therefore provides a symmetry breaking feature. Only in one of the illustrated positional states, which is shown in FIG. 8 the position and shape of the keying features 43, 43, 63 and 64 mutually match thereby allowing that the keying features 63, 64 of the limiter 60 axially slide or pass through the keying features 43, 44 of the dose tracking member 40.

In the present example the first and second keying features 63, 64 of the limiter 60 are provided and configured as a radially inwardly extending protrusion located near a distal end of the first and second legs 65, 66, respectively.

The first and second keying features 43, 44 of the dose tracking member 40 are provided as recesses or as axial through openings through the helically shaped keying structures 41, 42 on the outside circumference of the dose tracking member 40. There may be provided two separate keying structures 41, 42 on the outside circumference of the dose tracking member 40. As shown in FIG. 6, there is provided a first keying structure 41 in form of a first helical thread and a second keying structure 42 in form of a second helical thread.

The first and the second keying structures 41, 42 are arranged at a predefined axial offset 'O' as indicated in FIG. 6. Both, the first and the second keying structures can be encoded individually and independently. In typical examples the first and the second keying structures are encoded pairwise so as to provide simultaneous engagement or release with correspondingly shaped keying features of the limiter 60. The keying structures comprise keying features 43, 44 that match and align with correspondingly shaped keying features 63, 64 of the limiter 60 simultaneously. Typically, the offset 'O' is larger than or equal to the magnitude of the axial sliding motion of the limiter 60 from a blocking position b as shown in FIG. 3 and a dose dispensing position d or release position r as shown in FIG. 5. As it is further indicated in FIG. 6, the axial offset between the first and the second keying structure 41, 42 is smaller than the axial separation of 2 neighboring revolutions of the helically shaped keying structures 41, 42.

As seen for instance in axial direction, the second keying structure 42, hence the second helical thread is located at the predefined proximal offset 'O' from the first keying structure 41, i.e. from the first helical thread. Then and proximally adjacent to the second keying structure 42 there is provided a display portion 45 having a larger axial extension than the distance between or the axial offset between the convoluted keying structures 41, 42. The display portion 45 has printed numbers thereon to show up in a dose indicating window of the housing 10.

The keying features 63, 64 of the limiter 60 may be positioned at the same or identical axial position or they may be axially offset as shown in FIG. 5. Since the first and second keying features 63, 64 are in threaded or positive engagement with different circumferential portions of the first and the second keying structures 41, 42 this axial offset between the first and the second keying features 63, 64 is due to the pitch of the helically shaped keying structures 41, 42. As it is shown in FIGS. 6 and 7 the first keying structure 41 is located and positioned distally from the second keying structure 42. The radially inwardly extending keying feature 63 of the limiter 60 is axially positioned between the first and second keying structures 41, 42.

As the first keying features 63 of the limiter 60 aligns with the keying feature 43 of the first keying structure 41 also the second keying feature 64 of the limiter 60 aligns axially with a correspondingly shaped keying feature 44 of the second keying structure 42 (not shown). Since the keying features 43, 44 of the dose tracking member 40 are located at a predefined circumferential offset the second keying feature 64 of the limiter 60 move through the second keying feature 44 of the dose tracking member and will enter the intermediate space between the first and the second keying structure 42. A distal edge of the second keying feature 44 may then abut and engage with a proximal edge of the first keying structure 41. This engagement may limit the distally directed displacement of the limiter 60.

In order to allow and to support a dose dispensing action the axial offset 'O' between the first and the second keying structures 41, 42 is larger than or at least equal to an axial displacement of the limiter 60 and/or of the trigger 50 to disengage a clutch for switching the injection device 1 from the dose setting mode into the dose dispensing mode.

The mutually corresponding keying features 63, 64 and 43 and 44 of the limiter and the dose tracking member are arranged and configured such that during depressing of the trigger 50 and while the limiter 60 is displaced in distal direction a clutch of the windup expelling mechanism 2 disengages and releases before the second keying feature 64 of the limiter gets in axial abutment or axial engagement with the first keying structure 41 of the dose tracking member.

With almost all examples as described herein there are provided at least two pairs of keying features of the dose tracking member 40 and the limiter 60 that simultaneously engage and simultaneously disengage. In this way a redundant locking or blocking configuration between non-aligned and/or non-matching keying features of the dose tracking member 40 and the limiter 60 can be provided. In a locking configuration, in which the at least first and second keying features 63, 64 of the limiter 60 axially engage the first keying structure 41 and/or the second keying structure 42 of the dose tracking member 40 axial load acting on the trigger 50 and been transferred to the limiter 60 may homogeneously or equally distribute among the pairs of interengaging or interengaged keying features 43, 63 and 44, 64.

In the example as shown in FIGS. 3 to 10 the first and the second keying structures 41, 42 of the dose tracking member 40, hence a first and a second helical thread are arranged intertwined or in a convoluted way with a well-defined axial offset with respect to each other.

Figure 11:
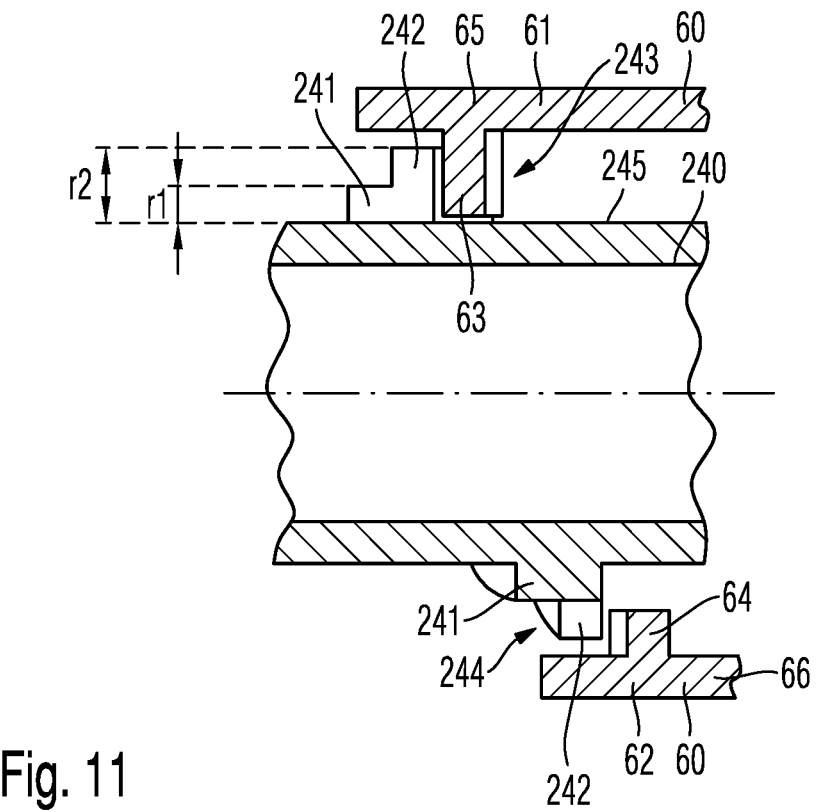
FIG. 11 shows a longitudinal cross-section through another example of a dose tracking member and a limiter in a proximal position.
Figure 12:
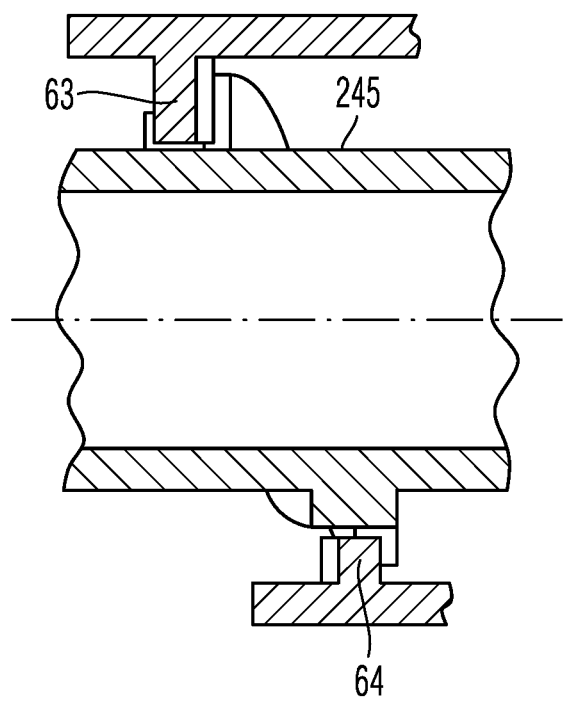
FIG. 12 shows the arrangement according to FIG. 11 with the limiter displaced towards the distal direction compared to FIG. 11.

In another example as shown in FIGS. 11 and 12 the first and the second keying structures 241, 242 are also provided on an outside circumference of a dose tracking member 240. The dose tracking member 240 also comprises a cylindrical or tubular shape. It may be engaged with the housing 10 by a slotted link 12 as described in connection with the example as shown in FIG. 2. The first and the second keying structures 241, 242 each comprise a helically shaped continues protrusion extending along the outer circumference of the dose tracking member 240. As it is apparent from FIGS. 11 and 12 the first keying structure 241 comprises a radial extension r1 that is smaller than a radial extension r2 of the second keying structure 242.

Both keying structures 241, 242 comprise at least one keying feature 243, 244. As shown in FIG. 11 the second keying structure 242, i.e. the one with the larger radial extension comprises a second keying feature 244 in form of an axial recess or axial slit exclusively in the outer most radial portion of the keying structure 242. Radially underneath the first keying structure 241 is void of such a recess or slit. The first keying structure 241 comprises a keying feature 243 in form of a recess or slit located elsewhere. As shown here, the keying feature 243 intersects both, the first keying structure 241 and the second keying structure 242 in axial direction. The keying feature 244 only axially intersected the outer most second keying structure 242 but has no overlap with the first keying structure 241.

The limiter 60 of which only the distal section is shown in FIGS. 11 and 12 comprises first and second engaging section 61, 62 with first and second keying features 63, 64. Also here, the first engaging section is provided on a first leg 65 and the second engaging section 62 is provided on a second leg 66. The first keying feature 63 comprises a radially inwardly extending protrusion at the first engaging section 61, hence at an inside facing surface of the first leg 65. Correspondingly, the second keying feature 64 comprises a radially inwardly extending protrusion provided at an inside facing portion of the second engaging section 62 and hence at the second leg 66. As it is apparent from FIGS. 11 and 12 the keying features 63, 64 have different radially inwardly protruding dimensions. The radial extension of the first keying feature 63 is larger than the radial extension of the second keying features 64.

Only in the configuration as shown in FIG. 11 the first keying features 63 of the limiter 60 is aligned with the first keying feature 243 intersecting and extending through both, the first keying structure 41 and the second keying structure 42. In the same configuration it is the second keying feature 64 of the limiter 60 that aligns with the second keying feature 244 of the second keying structure 242. In this configuration the limiter 60 with its keying features 63, 64 is allowed to pass the keying structures 241, 242 in axial direction, hence towards the distal end 5 of the injection device 1.

In another configuration, wherein the dose tracking member 240 would be rotated by 180° compared to the configuration as shown in FIGS. 11 and 12 the first keying feature 63, hence the first protrusion of the limiter 60 would be aligned with the second keying feature 244 of the dose tracking member. Since the radial depth of the recess of the second keying feature 244 is smaller than the radially inwardly protruding extension of the first keying feature 63 the first keying feature 63 would be hindered to pass through the keying feature 244. As a consequence, the radially inwardly protruding keying features 63 would get in axial abutment with a proximal abutment face of the first keying structure 241. The distally directed displacement of the limiter 60 would be blocked.

The FIGS. 11 and 12 are illustrative of an example, wherein the second keying structure 242 is radially offset from the first keying structure 241. Here, the first and the second keying structures 241, 242 may axially overlap or may axially coincide. In effect, the total axial elongation on the axial space occupied on the outer circumference of the dose tracking member 240 can be reduced compared to the example as shown in FIG. 6. The axial extension or axial width of a circumferential portion of the first and the second keying structures 241, 242 can be smaller than the axial dimensions of a circumferential portion of the first and the second keying structures 41, 42 of the dose tracking member 40 of FIG. 6.

Consequently, the axial extension of a display portion 245 axially adjacent to the first and the second keying structures 241, 242 can be increased. Numbers printed in or on the display portion 245 can be enlarged while keeping the pitch of the helically shaped keying structures 241, 242 in the same range or at the same level compared to the keying structures 41, 42 of the example as shown in FIGS. 3 to 10.

In the examples as shown in FIGS. 1 to 12 and 15 to 33 the dose tracking member 40, 240 provides a double function. Axially between neighboring convolutions of the helically shaped keying structures 41, 42, 241, 242, there is provided a display portion 45, 245 that has sequence of numbers on an outside facing surface. Therefore, the dose tracking member 40, 240 also serves as a number sleeve 70 with a helical sequence of consecutive numbers printed thereon. The numbers show up in a dosage window of the main housing component 14 as the number sleeve 70 or dose tracking member 40, 240 is rotated in dose incrementing or dose decrementing direction.

Figure 13:
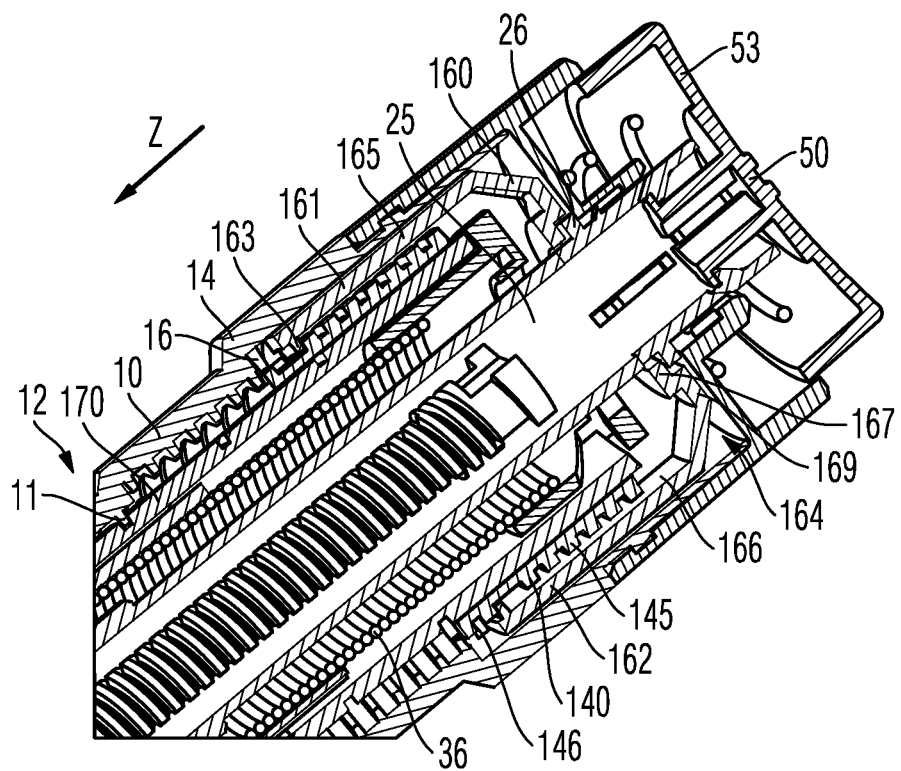
FIG. 13 shows another example of a proximal portion of an injection device in a perspective view.
Figure 14:
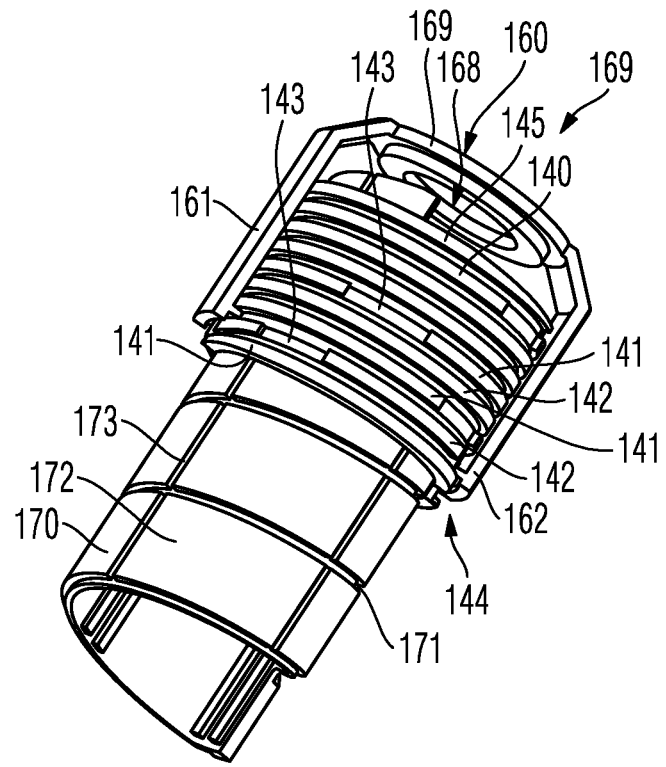
FIG. 14 shows the dose tracking member, a number sleeve and the limiter according to FIG. 13 in a perspective and isolated view.
Figure 15:
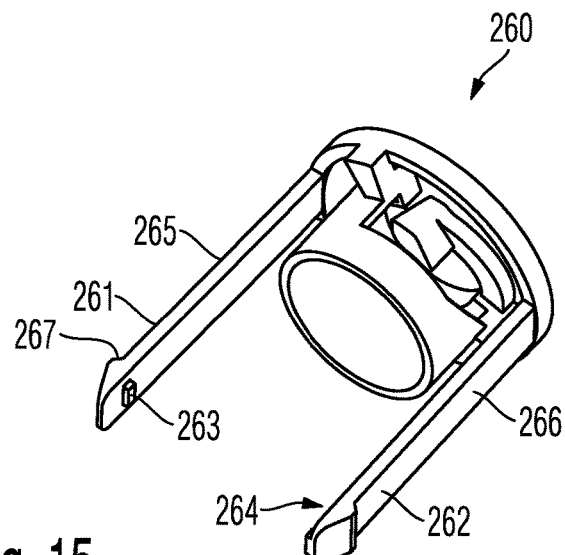
FIG. 15 shows an isolated view of another example of a limiter.

In the example as shown in FIGS. 13 and 14 there is provided a separate number sleeve 170 in addition to a dose tracking member 140. The number sleeve 170 is threadedly engaged with the housing 10. There is provided a slotted link 12 between the housing 10 and the number sleeve 170. The slotted link 12 comprises a radially inwardly extending threaded section 11 that is threadedly engaged with a correspondingly shaped helically wound threaded section 171 on the outer circumference of the number sleeve 70. The threaded section 171 is a recessed threaded section and extends radially inwardly from the outside surface of the number sleeve 170.

As shown in FIG. 14, the number sleeve 170 comprises a display portion 172 between axially neighboring convolutions of the threaded section 171. Here and in comparison to the examples as shown in FIGS. 1 to 12 the axial dimension of the display portion 172 is comparatively large since the number sleeve 170 comprises only a single threaded section 171. Also here, the display portion 172 is provided with a helical sequence of consecutive numbers that show up in the dosage window of the housing 10 of the injection device 1.

The dose tracking member 140 also comprises a sleeve like shape. It is axially confined in a proximal portion of the main housing component 14. The dose tracking member 140 comprises a circumferential engaging section 146 that is axially engaged with a correspondingly shaped engaging section 16 at the inside of the sidewall of the housing 10. Here, the engaging section 146 provided at a distal end of the dose tracking member 140. The engaging section 146 is configured to rotate while in engagement with the engaging section 16 of the housing 10. The engaging section 16 comprises a radially inwardly extending protrusion or a correspondingly shaped rib engaging with a the groove shaped engaging section 146 of the dose tracking member 140. In this way the dose tracking member 140 is free to rotate relative to the housing 10. By means of the mutual engagement of the engaging sections 146 and 16 the dose tracking member 140 is axially fixed to the housing 10.

The dose tracking member 140 is permanently rotationally locked to the number sleeve 170. This interlock is provided by a keyed engagement of the number sleeve 170 and the dose tracking member 140. The number sleeve 170 comprises an axially extending keying structure 173 extending in axial direction on the outer circumference of the number sleeve 170. In the example as shown in FIG. 14 the keying structure 173 comprises an axially extending recessed slot. The dose tracking member 140 enclosing the outer circumference of the number sleeve 170 comprises a correspondingly shaped radially inwardly extending pin or a respective protrusion that rests inside the keying structure 173.

In this way, the number sleeve 170 is free to slide axially relative to the dose tracking member 140. Due to the keyed engagement between the number sleeve 170 and the dose tracking member 140 the dose tracking member 140 is permanently rotationally locked to the number sleeve 170. A rotation of the number sleeve 170 during a dose setting procedure or during dose expelling is therefore equally transferred to a respective rotation of the dose tracking member 140. As indicated on FIG. 14 the dose tracking member comprises a first keying structure 141 and a second keying structure 142. Here, the first and the second keying structures 141, 142 are equidistantly arranged in axial direction. Hence, the axial offset between the first keying structure 141 and the second keying structure 142 substantially equals the axial offset between the second keying structure 142 to the first keying structure 141. Furthermore, the dose tracking member 140 is void of a display portion. The overall axial extension of the dose tracking member 140 can be reduced and miniaturized compared to the example as described in connection with FIGS. 1 to 12 or in connection with any one of the FIGS. 15 to 33.

Apart from that the function of the first and second keying structures 141, 142 is substantially identical to the function of the keying structures 41, 42 described above in connection with FIGS. 1 to 12. The first keying structure 141 comprises a first outer thread and the second keying structure 142 comprises a second outer thread. The first and the second keying structures 141, 142 comprise an identical pitch. The first keying structure 141 comprises a first keying feature 143. The second keying structure 142 comprises a second keying feature 144. The first and second keying features 143, 144 are configured as an axial recess, as an axial slot or as an axial interruption of the respective keying structures 141, 142.

The limiter 160 also comprises a first engaging section 161 and a second engaging section 162. The first engaging section 161 is provided with a first keying feature 163 extending radially inwardly from a distal free end of the first engaging section 161. The first engaging section 161 comprises a first leg 165 extending in distal direction from a proximal end section 169 of the limiter 160.

In a similar way also the second keying feature 164 is provided near or on a distal free end of the second engaging section 162. The second engaging section 162 comprises a second leg 166. Also the second leg 166 and the second engaging section 162 extend substantially in distal direction from the proximal end section 169 of the limiter 160. As illustrated in FIG. 14, the proximal end section 169 comprises a flat an annular structure with a central through opening 168. The proximal end section 169 resembled a flat disk. A border 167 of the through opening 168 has a stepped down recess to receive a radially outwardly extending flange 26 on an outside surface of a drive sleeve 25.

The drive sleeve 25 extends axially through the number sleeve 170 and axially through the dose tracking member 140. The flange 26 is in axial abutment with the border 167 of the through opening 168. As shown in FIG. 13, the flange 26 is located proximally from the through opening 168. A distally facing age of the flange 26 is in axial abutment with a proximally facing edge of the border 167. As further illustrated in FIG. 13 an inside facing surface of the button portion 53 of the trigger 50 is axially engageable with a proximal end face 27 of the drive sleeve 25. In this way and by depressing the trigger 50 in distal direction the drive sleeve 25 is displaceable in distal direction. By means of the axial abutment of the flange 26 with the border 167 a distally directed advancing motion of the drive sleeve 25 is transferred into a corresponding distally directed sliding displacement of the limiter 160. This distally directed displacement of the limiter 160 is only allowed and possible if the keying features 163, 164 thereof are aligned with correspondingly shaped and correspondingly positioned keying features 143, 144 of the dose tracking member 140.

The limiter 160 as shown comprises at least two engaging sections, namely with a first engaging section 161 and a second engaging section 162. It is possible to have three or more equidistantly arranged engaging sections 161, 162 arranged around the outer circumference of the dose tracking member 140.

In FIGS. 15 to 22 another implementation of limiter 260 and the trigger 250 is shown. Here, the trigger 250 combines the trigger 50 and the handle 90 as described with regards to the example of FIG. 1 or 2. The combined trigger/handle 250 comprises a sleeve like shape with a closed bottom 251 forming a proximal end face 252. The trigger 250 comprises a sidewall 253. The sidewall 253 comprises a distal end section 254. The trigger 250 comprises a cup shaped receptacle, wherein the sidewall 253 and the bottom 251 cover and enclose a proximal end 4 of the injection device 1. The trigger 250 is rotatably mounted to the drive sleeve 25. The trigger 250 comprises an axially extending stem 255 extending in the distal direction from the inside of the bottom 251. The stem 255 comprises a radially outwardly extending flange section 256 by way of which the trigger 250 is axially engaged with the drive sleeve 25. The drive sleeve 25 comprises radially inwardly extending protrusions 28 in axial engagement with the outwardly extending flange section 256.

There is further provided an interface member 210 that is selectively rotationally engageable with the drive sleeve 25. At an inside surface of the sidewall 253 and adjacent to the button 251 there is provided a splined feature 258 of the trigger 250 permanently rotationally engaged with the interface member 210. The interface member 210 comprises a correspondingly shaped splined feature 211 on its outer circumference. The interface member 210 is of disk-like shape. The interface member 210 further comprises an axial central through opening 212 to receive the drive sleeve 25 and the stem 255 axially there through. On the inside of the through opening 212 there is arranged another splined feature 214 rotationally locked or rotationally lockable to a correspondingly shaped splined feature 29 on the outer circumference of the drive sleeve 25.

Figure 16:
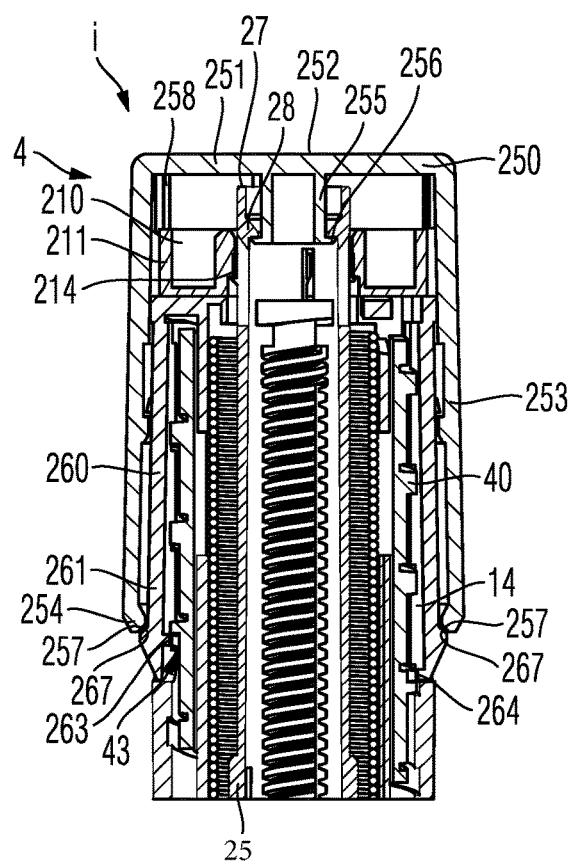
FIG. 16 shows a cross-section of an another example of an injection device with a limiter according to FIG. 15 and with the trigger in an idle position.
Figure 17:
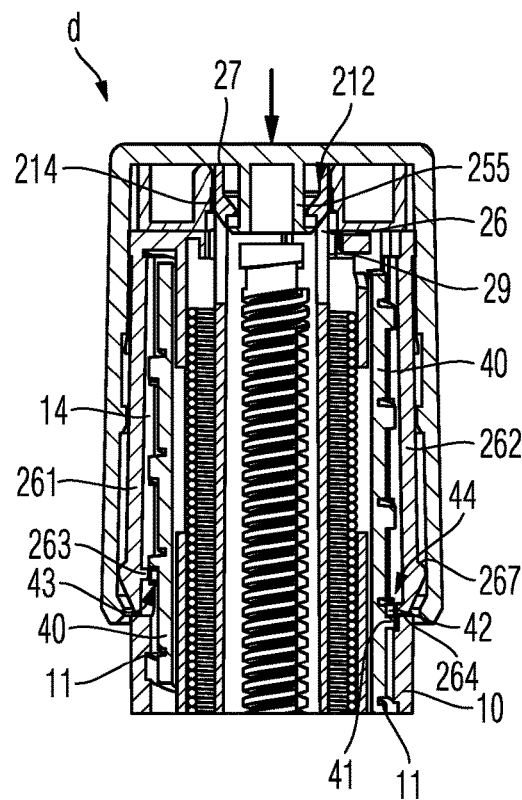
FIG. 17 shows a cross-section of the device according to FIG. 16 with the trigger depressed in distal direction.

In the idle position i of the trigger 250 as shown in FIG. 16 the splined features 214, 29 are in engagement. Hence, the splined features 29, 214 axially overlap. In this way, the interface member 210 is rotationally locked to the drive sleeve 25. Since the interface member 210 is permanently rotationally locked to the trigger 250 via the splines 211 and 258 the trigger 250 is rotationally locked to the drive sleeve 25 as long as the trigger 250 is in the proximal idle position i. By depressing the trigger 250 in distal direction so as to arrive in the dose dispensing position the inside facing portion of the button 251 gets in axial abutment with the proximal end face 27 of the drive sleeve 25. In this way the drive sleeve 25 is displaced towards the distal direction. Consequently and since the interface member 210 is axially locked or axially connected to the limiter 260 the splined engagement of the interface member 210 and the drive sleeve 25 is released as indicated in FIG. 17.

The distally directed displacement of the drive sleeve 25 is such that the splined features 29 arrive at a distal position in which they disengage from the splined features 214. In this way and when reaching the dose dispensing position d as indicated in FIG. 17 the drive sleeve 25 is free to rotate under the action of the mechanical energy reservoir 75 while the trigger 250 is held in a nonrotating dose dispensing position, e.g. through the action of a thumb of a user.

Also with the example as shown in FIGS. 15 to 22 the limiter 260 is rotationally locked to the housing 10, in particular to the main housing component 14. The limiter 260 comprises a first engaging section 261 with a radially inwardly extending first keying feature 263. The first keying feature 263 and the first engaging section 261 are provided on a first axially extending leg 265. The second keying feature 264 is located on a radial inside of an axially extended second leg 266 forming a second engaging section 262. Also here, the first and the second engaging sections 261, 262 as well as the respective keying features 263, 264 are located at diametrically opposite to each other and with regard to the cylindrical geometry of the dose tracking member 40. The dose tracking member 40 is shown in a partially cut view in FIG. 21. In a real example, the dose tracking member 40 comprises a tubular or cylindrical shape with a closed outer cylindrical sidewall.

The dose tracking member 40 also provides a number sleeve 70. The dose tracking member 40 comprises a first keying structure 41 with at least a first keying feature 43. Typically, the dose tracking member 40 also comprises a second keying structure with at least a second keying feature 44. Here, the keying features 41, 42 are provided and arranged as radially outwardly extending helically-shaped protrusions on the outer circumference of the dose tracking member 40. As shown in FIG. 21, the first keying structure 41 and the second keying structure 42 are in direct axial abutment. The first keying structure 41 comprises a first keying feature 43 inform of a radial recess or radial gap. Also the second keying structure 42 comprises a second keying feature 44 in the form of a radial recess or gap. The radially extending recesses and hence the first and the second keying features 43, 44 are configured to receive the radially inwardly extending keying features 263, 264 of the limiter 260.

In the configuration as shown in FIGS. 16 and 17 the keying features 263, 264 protrude radially inwardly and may extend through a correspondingly-shaped through opening or recess in the sidewall of the main housing component 14. In order to allow and to support a distally directed axial displacement of the trigger 250 the protrusions and hence the first and the second keying features 263, 264 at least temporally enter the correspondingly shaped keying features 43, 44 of the first and the second keying structures 41, 42, respectively. If properly aligned, the mutually engaging keying features 43, 44, 263, 264 allow for a radially inwardly directed deflection or movement of the first and second engaging sections 261, 262 of the limiter 260. A radially inwardly directed deflection or movement of the first and second engaging section 261, 262, is governed and initiated by mutually corresponding beveled sections 267, 257 of the trigger 250 and of the limiter 260, respectively.

In the configuration as shown in FIGS. 16 and 18, the distal end section 254 of the trigger 250 is in axial and beveled abutment with a radially outwardly protruding beveled section 267 of the first and of the second engaging sections 261, 262. The mutual abutment of the beveled section 267 with a correspondingly shaped counterpart section 257 at the distal end of the trigger 250 is shown in FIG. 18. Since the counterpart section 257 comprises an annular and closed shape at the distal end of the cup-shaped trigger 250, the counterpart section 257 is rather stiff. As illustrated in FIG. 18, the outer diameter or the radial distance between the beveled sections 267 of the first and of the second engaging sections 261, 262 is larger than the inner or inside distance between correspondingly shaped and oppositely located portions of the counterpart section 257.

In this way, and as long as the first and/or the second engaging sections 261, 262 are hindered from deflecting radially inwardly a distally directed movement of the trigger 250 towards the dose dispensing position d is effectively blocked. In FIG. 18, such a blocking configuration and hence a blocking position of the limiter 250 is shown. The keying feature 263 of the first engaging section 261 is in radial abutment with the first keying structure 41 of the dose tracking member 40. As illustrated in FIG. 16. The same is also valid for the second keying feature 264 of the second engaging section 262. As the dose tracking member 40 is turned and reaches an allowable positional state a respective keying feature 43 will be aligned radially inwardly to the first keying feature 263. Also, the second keying feature 264 will be aligned with the second keying feature 44 of the dose tracking member 40.

As the mutually corresponding keying features 43, 263 and 44, 264 of the dose tracking member 40 and the limiter 260 correctly align the first and second engaging sections 261, 262 will be allowed to deflect radially inwardly under the action of the distally advancing trigger 250. This radially inwardly directed motion is due to the beveled or tilted slope of the mutually engaging counterpart section 257 of the trigger 250 and the beveled section 267 on the outside surface of the first and second engaging sections 261, 262, respectively.

With the radially inwardly directed deflection of the first engaging section 261 as shown in FIG. 19 the trigger 250 is enabled to reach its distal dose dispensing position d as shown in FIG. 20. In this position the radially inwardly extending counterpart section 257 is located distally from the radially outwardly extending beveled section 267 of the first and the second engaging sections 261 and 262 respectively.

Once the trigger 250 has reached the distal dose dispensing position d as shown in FIG. 20 the radially inwardly protruding or radially inwardly extending counterpart section 257 of the trigger 50 is entirely located distally from the beveled section 267 of the limiter 260. As a consequence, the first and second engaging sections 261, 262 and hence the keying features 263, 264 are allowed to return into their initial position in which the innermost portion of the keying features 263, 264 of the limiter 260 are located radially outside the keying structures 41, 42. In this way, a frictionless or contactless configuration of the keying features 263, 264 with regard to the keying structures 41, 42 can be obtained, thus allowing the dose tracking member 42 to return into its initial configuration during the dose dispensing procedure.

As seen from the proximal end towards the distal end the beveled sections 267 of the first and the second engaging sections 261, 262 of the limiter 260 extend radially outwardly in distal direction. In the initial or idle position i as shown in FIG. 18 the correspondingly beveled counterpart section 257 of the trigger 250 is located proximally from the beveled section 267. As the trigger 250 and hence the counterpart section 257 advances in distal direction, hence downwards in FIGS. 19 and 20. The first and the second engaging sections 261, 262 experience a radially inwardly directed deflection.

This deflection is only possible if the respective keying features 263, 264 are circumferentially and axially properly aligned with the correspondingly shaped keying features 43, 44 of the dose tracking member 40. This is shown in more detail in FIG. 22. There, the first keying feature 263 of the first engaging section 261 is at the same axial and the same circumferential position as the correspondingly shaped first keying feature 43 of the dose tracking member 40. The first keying feature 43 is configured and shaped to receive the protrusion of the first keying feature 263 so as to enable and to support a radially inwardly directed deflection of the respective engaging section 261.

Also with the example of FIGS. 15 to 22 the pairs of mutually corresponding engaging features 43, 263 and 44, 260 4 simultaneously engage or simultaneously disengage. In this way both legs 265, 266 or both engaging sections 261, 262 either provide an axial bearing for the distal end section of the trigger 250 or both engaging sections 261, 262 simultaneously deflect radially inwardly so as to give way for the distally advancing trigger 250.

As it is further shown in FIGS. 16, 17, and in FIG. 22 the elastically deformable legs 265, 266 are not strictly oriented in axial direction when in an original or unbiased state. Rather, they extend at a slight radially outwardly extending angle a with regard to the axial direction or longitudinal direction of the housing 10. In this way, and as indicated in FIG. 22 to the elongation of the legs 265, 266 is oriented at a predefined angle a outwardly from the longitudinal direction of the housing 10 or the dose tracking member 40. The first and/or the second leg 265, 266 may extend at a small but distinct angle a. Alternatively, the first and the second leg 265, 266 may extend substantially parallel with respect to each other but at a predefined clearance or at a predefined radial distance from the dose tracking member 40.

In this way, there is formed and provided a radial gap or radial clearance between the keying features 263, 264 of the limiter 260 and the keying structures 41, 42 of the dose tracking member when there is no distally directed pressure applied to the trigger 50, e.g. during dose setting. The radially inwardly extending protrusions and hence the first and the second keying features 263, 264 of the limiter 260 are in a contactless configuration relative to the keying structures 41 or 42 on the outside surface of the dose tracking member 40. Hence, during dose setting and while the dose tracking member 40 is subject of a rotation there is no friction between the keying features 263, 264 of the limiter 260 and the keying structures 41, 42 of the dose tracking member 40. The dose tracking member 40 and hence the number sleeve 70 can be subject to a helical motion relative to the housing 10 with a comparatively low degree of dynamic friction.

In FIGS. 23 to 33 another example of a limiter 360 to cooperate with a dose tracking member 40 is illustrated. With this example, the injection device 1 comprises a proximal end with a rotatable handle 90. There is further provided a trigger 50 as already described in connection with FIGS. 1 through 10. As shown in longitudinal cross-section of FIGS. 23 and 24, the limiter 360 comprises a rim shaped or annular shaped proximal end 369 with an axial through opening 376 extending there through. The limiter 360 also comprises a first and axially elongated engaging section 361 and a second axially elongated engaging section 362. At an inside facing portion near a distal end of the first and the second engaging sections 361, 362, there are provided first and second keying features 363, 364, respectively.

Figure 23:
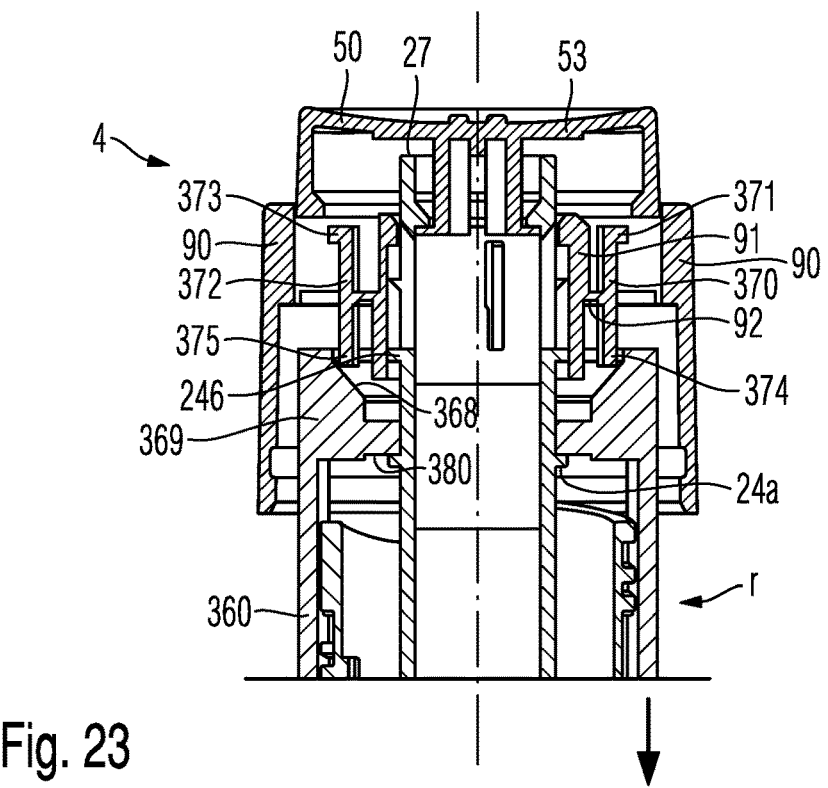
FIG. 23 shows a cross-section of another example of an injection device with the dose tracking member in an allowable positional state.
Figure 24:
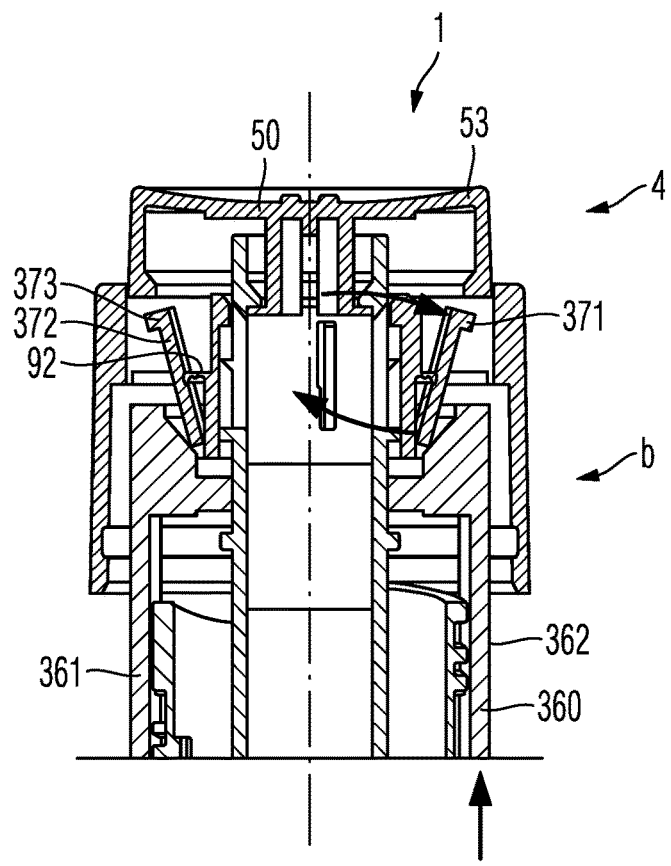
FIG. 24 shows a cross-section of the example of FIG. 23 with the limiter displaced towards the proximal end.
Figure 25:
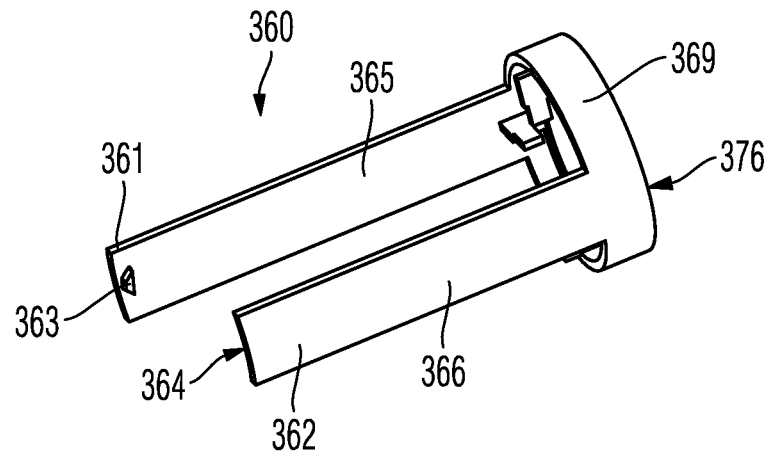
FIG. 25 is an isolated perspective view of the limiter.

Also here, the first engaging section 361 is formed by a first leg 365. The second engaging section 362 is formed by a second leg 366. The legs 365, 366 and hence the first and the second engaging sections 361, 362 are located at diametrically opposite locations with regard to the tubular shape of the dose tracking member 40 located there between. Alternative Contraryto the examples described before the limiter 360 is axially displaceable between a distal release position r as shown in FIG. 23 and a proximal blocking position b as shown in FIG. 24. In the blocking position b and hence when displaced proximally from the release position r the limiter 360 is configured to engage with two blocking elements 370, 372. Movement of the limiter 360 is not directly driven by a movement of the trigger 50. Here, an axial movement of the limiter 360 is exclusively triggered and governed by the mutual interaction between the limiter 360 and the dose tracking member 40. When in a blocking configuration or blocking position b movement of the trigger 50 is effectively blocked by the limiter 360.

The blocking elements 370 are located axially beneath the trigger 50. Both blocking elements 370, 372 comprise a proximal end 371, 373. In an initial or idle configuration, the blocking elements 370, 272 extend along the axial direction or axial elongation of the housing 10. As the limiter 360 is shifted or displaced towards the proximally located blocking position b the proximal end section 369 thereof simultaneously engages with the blocking elements 370, 372 in such a way that the proximal ends 371, 373 thereof are moved radially outwardly.

In this way, the proximal ends 371, 373 of the blocking elements 370, 372 extend outwardly and enter a free space, which is normally occupied by the button portion 53 of the trigger when reaching the dose dispensing position d. In the blocking position b the proximal ends 371, 373 of the blocking elements 370, 370 are configured to impede a further distally directed advancing motion of the trigger 50. Hence, the trigger 50 engages with the blocking elements 370, 372 and is hindered to reach the dose dispensing position d.

The blocking elements 370, 372 may be integrally formed with the handle 90. They may be flexibly or resiliently connected to an inner sleeve 91 of the handle 90. The inner sleeve 91 is rotationally supported on the drive sleeve 25. It may be rotationally disengaged from the drive sleeve 25 to allow for a rotation of the handle 90 relative to the drive sleeve 25 during dose setting as well as during dose dispensing.

The blocking elements 370, 372 may be integrally formed or may be molded to the inner sleeve 91. The blocking elements 370, 372 comprise an axial midsection, that is connected to an outer circumference of the inner sleeve 91. The blocking elements 370, 372 are connected to the inner sleeve 91 by means of a radially outwardly extending connecting link 92 so that the blocking elements 370, 372 are located at a predefined radial distance from the outer circumference of the inner sleeve 91. This allows for a pivoting or rotating motion of the blocking elements 370, 372 with a pivot axis coinciding with the connecting link 92 as illustrated in FIGS. 23 and 24.

The proximal end section 369 of the limiter 360 comprises a beveled section 368 at an inside facing sidewall portion. The beveled section 368 is in axial abutment or close to an axial abutment with the distal end 374, 375 of the blocking elements 370, 372. The beveled section 368 extends radially inwardly in distal direction. As the limiter 360 is moved from the release position as shown in FIG. 23 and towards the blocking position as shown in FIG. 24 the beveled section 368 engages with the distal ends 374, 375 of the blocking elements 370, 372.

Consequently, the distal ends 374, 375 become subject to a radially inwardly directed displacement. This displacement leads to a rotation or pivoting motion of the blocking elements 370, 372, such that their proximal ends 371, 373 move radially outwardly. The blocking elements 370, 372 resiliently pivot with the connecting link 92 as a pivot axis. The pivot axis extends tangentially or circumferentially, hence perpendicular to the elongation of the housing 10.

The blocking elements 370, 372 are resiliently supported on the handle 90. In the region and by means of the connecting link 92 the blocking elements 370, 372 are resiliently deformable or pivotable against a restoring force. As the limiter 360 returns into its distal release position r the blocking elements 370, 372 return into their initial configuration as shown in FIG. 23, in which the blocking elements 370, 372 are substantially aligned in an axial direction.

Figure 26:
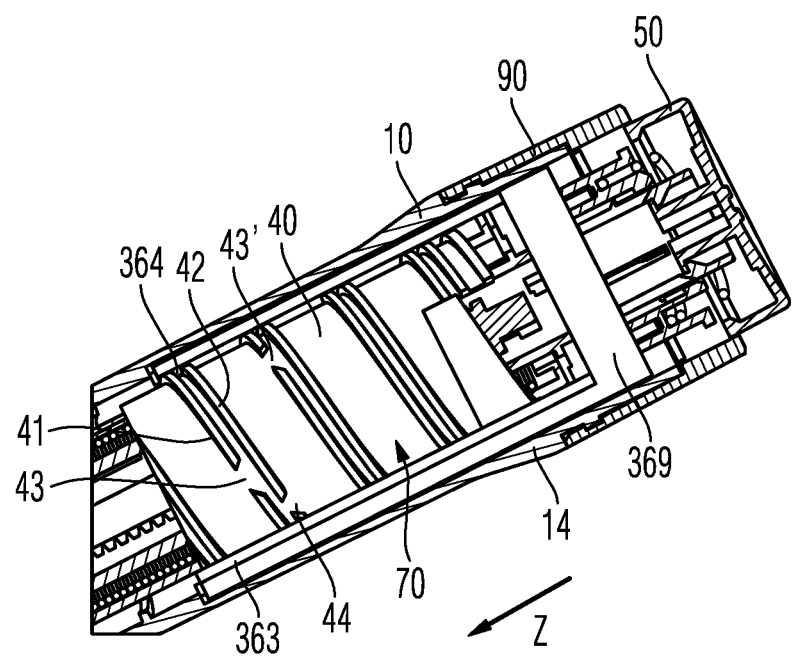
FIG. 26 is a perspective and partially cut view of the device according to FIGS. 23 to 25.

Alternative to the example as shown in FIGS. 1 to 22 the limiter 360 is axially displaceable inside the main housing component 14 between the distally located release position r and the proximally located blocking position b. An axial displacement of the limiter 360 is governed and conducted by mechanical interaction with the dose tracking member 40. The dose tracking member 40 comprises a tubular-shaped sleeve. The dose tracking member 40 as shown in the example of FIG. 26 is substantially identical to the dose tracking member 40 as described in connection with FIGS. 1 to 6. It is engaged with the housing 10 by means of a slotted link 12. In the present example the dose tracking member comprises a first keying structure 41 and a second keying structure 42 that extend parallel. Both keying structures 41, 42 comprise a helical thread on the outside surface of the dose tracking member 40. Here, the dose tracking member 40 also provides and constitutes a number sleeve 70.

The first keying structure 41 comprises at least a first keying feature 43 in form of a recess, an axial slot or gap in the outer thread. Also the second keying structure 42 comprises a second keying feature 44, which is likewise configured in the form of a recess, an axial slot or gap in the respective outer thread. Contrary to the examples as shown in FIGS. 1 to 6 the keying features 43, 44 of the dose tracking member 40 as shown in FIG. 26 comprise a chamfered end section 49 as shown in detail in FIG. 27. In FIGS. 27 to 31 the distal axial direction points downward and the circumferential or tangential direction of the dose tracking member 40 is aligned horizontally.

The keying features 363 and 364 of the limiter 360 are configured to engage and to interact with the correspondingly shaped keying features 43, 44 of the dose tracking member 40. As shown in FIGS. 27 through 31 the keying features 363, 364 comprise radially inwardly extending protrusions on an inside facing surface of the first leg 365 and second leg 364, respectively. The first keying feature 363 comprises a beveled edge 367 as seen in tangential direction. The beveled edge 367 is shaped to conform with the chamfered end section 49 of the first keying structure 41.

Figure 27:
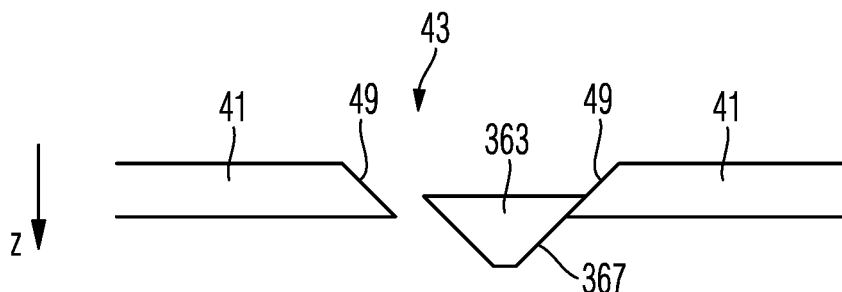
FIG. 27 is a schematic illustration of the interaction between the keying features of the limiter and the dose tracking member.
Figure 28:
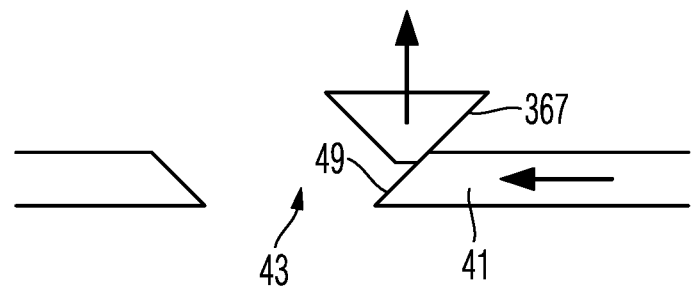
FIG. 28 shows the component of FIG. 27 with the keying feature of the limiter displaced in proximal direction.
Figure 29:
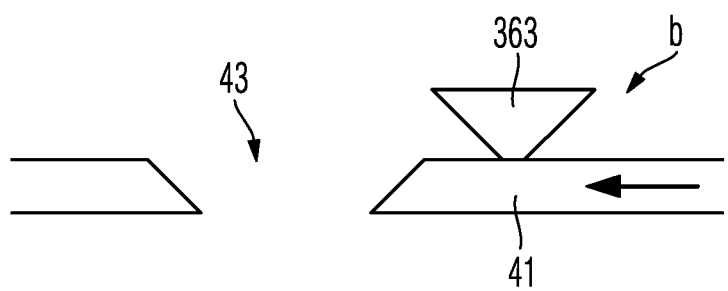
FIG. 29 is illustrative of a further configuration of the keying features of FIGS. 27 and 28.

In an initial configuration as shown in FIG. 27 the first keying feature 363 at least partially overlaps in axial direction with the chamfered end section 49 of the first keying structure 41. In this configuration the first keying structure 363 extends radially inwardly and into the recess, slot or gap of the first keying structure 41. As the dose tracking member 40 is subject to a rotation the beveled edge 367 of the first keying feature 363 slides along the correspondingly-shaped chamfered edge 49 of the first keying structure 41. As a consequence, the first keying feature 366 and hence the entire limiter 360 experiences a proximally directed displacement until the entirety of the keying features 363 is located proximally of the chamfered end section 49 as shown in FIG. 29.

In this configuration the limiter 360 has reached a blocking position b. In this configuration a distal edge of the first keying feature 363 is in axial abutment with a proximal edge of the first keying structure 41. In this configuration and due to the axial abutment of the keying feature 363 of the limiter 360 with the keying structure 41 of the dose tracking member 40 a distally directed displacement of the limiter 360 is effectively blocked and prevented. Accordingly and due to the displacement of the limiter 360 towards the proximal blocking position b the blocking elements 370, 372 have reached a respective blocking configuration as shown in FIG. 24 in which they effectively impede a distally directed depression of the trigger 50.

Figure 30:
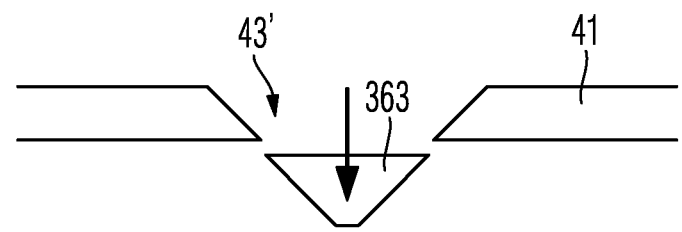
FIG. 30 shows a further configuration of the keying features of the limiter and the dose tracking member.
Figure 31:
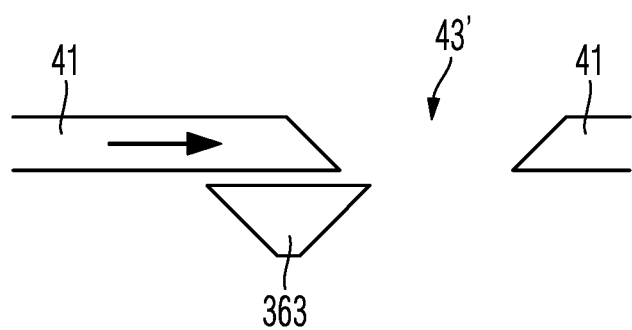
FIG. 31 is illustrative of a further configuration of the keying features of the limiter and the dose tracking member.

It is only when the dose tracking member 40 is dialed or rotated further and until another first keying structure 43' is aligned with the first keying structure 363 of the limiter 360 that the limiter 360 is displaceable in distal direction, and downwardly in FIG. 30. A movement of the limiter 360 in distal direction is induced by the resilient restoring force provided by the blocking elements 370, 372. Here, the distal ends 374, 375 exert a radially outwardly directed restoring force onto the beveled section 368 of the proximal end 369 of the limiter 360. As soon as the first keying structure 363 is properly aligned with the first keying feature 43 'of the dose tracking member 40 the limiter 360 will be pushed or will return at least into the configuration as shown in FIG. 27. Simultaneously, also the second keying structure 364 will be axially aligned with a corresponding second keying feature 44 'of the dose tracking member 40. Consequently, the limiter 360 will be pushed distally towards and/or into the release configuration r as shown in FIG. 27.

In the release configuration r a distally directed depression of the trigger 50 is enabled. As it is apparent from FIGS. 32 and 33 a distally directed depression of the trigger 50 leads to a corresponding distally advancing motion of the drive sleeve 25. Here, the bottom of the button portion 53 of the trigger 50 axially abuts against the proximal end face 27 of the drive sleeve 25. Furthermore and as shown in FIGS. 23, 24, 32 and 33 the drive sleeve 25 comprises two radially outwardly extending engaging sections 24a, 24b.

Both engaging sections 24a, 24b comprise a radially outwardly extending rim or protrusion rib. The engaging section 24a is located distally compared to the position of the engaging section 24b. Axially between the two engaging sections 24a, 24b there is located at least one radially inwardly extending tappet 380 protruding radially inwardly from the annular shaped proximal end section 369 of the limiter 360. The tappet 380 protrudes radially inwardly from the annular section 369 of the limiter 360 It is in radial engagement with the outer circumference of the drive sleeve 25. The tappet 380 is configured to selectively axially engage with the distally located engaging section 24a and with the proximally located engaging section 24b.

Figure 32:
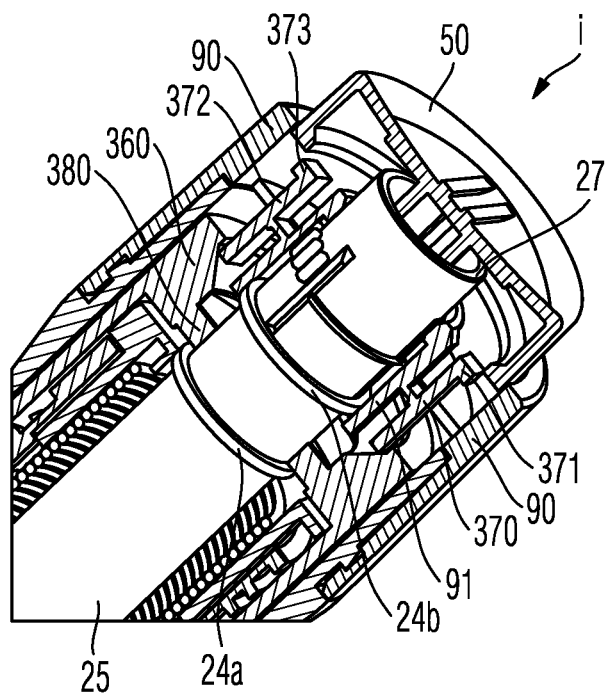
FIG. 32 shows the proximal end of the injection device with the keying features of FIGS. 23 to 31 with the trigger in an idle position and FIG. 33 shows the device according to FIG. 32 with the trigger in the dose dispensing position.
Figure 33:
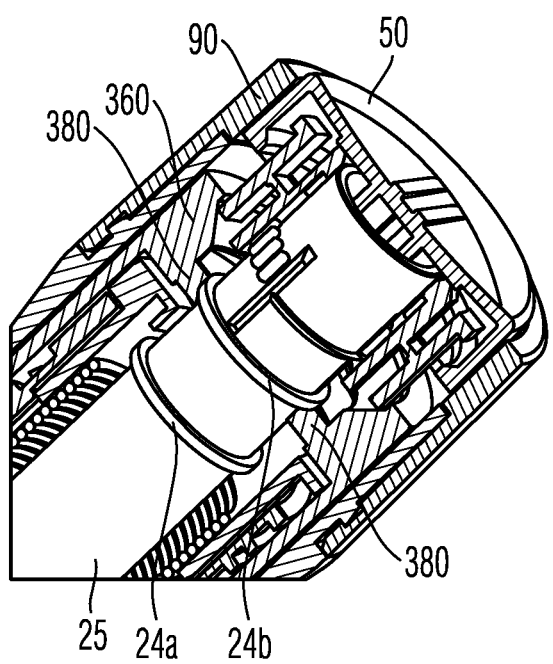

In the release configuration as shown in FIGS. 23 and 32 in which the first keying feature 363 at least partially axially overlaps and engages with the first keying structure 41 of the dose tracking member 40 the trigger 50 is fully depressible. As the trigger 50 is depressed and displaced towards the distal end 5 of the injection device 1 the drive sleeve 25 is also displaced distally until the proximally located engaging section 24b axially abuts the tappet 380. This abutment configuration is attained before the trigger 50 reaches the dose dispensing position d. By means of the axial engagement of the tappet 380 with the engaging section 24b the limiter 360 will be displaced and moved in distal direction as the trigger 50 is displaced further in distal direction. This is illustrated in FIG. 33.

Due to the axial engagement between the tappet 380 and the engaging section 24b the first keying structures 363 entirely traverses the first keying structure 43 of the first keying structure 41 of the dose tracking member 40. As the trigger 50 reaches the dose dispensing position d the first keying structure 363 is located in its entirety distally from the first keying structure 41. In this configuration and during the subsequently ongoing dose dispensing procedure the dose tracking member 40 and hence the keying structure 41 may be subject to a dose decreasing rotation as shown by the horizontal arrow in FIG. 31.

When upon completion of the dose dispensing the trigger 50 is released it will return into its initial or idle position i as indicated in FIG. 32. Since the trigger 50 is axially engaged with the drive sleeve 25 the proximally directed displacement of the trigger 50 leads to a corresponding proximally directed movement of the drive sleeve 25. Consequently, the distally located engaging section 24a axially abuts with the tappet 380. The engaging section 24a, and in particular a proximally facing side edge thereof axially abuts a distally facing edge of the tappet 380. In this way, the tappet 380 and the entire limiter 360 is dragged in the proximal direction under the action of the proximally returning drive sleeve 25 until the limiter 360 reaches the initial release position r as indicated in FIG. 27.

Even though there is shown only the interaction between a first keying feature 363 with a first keying structure 41 of the dose tracking member 40 in the sequence of FIGS. 27 to 31 the dose tracking member 40 and the limiter 360 are in a pairwise mechanical engagement by means of a first pair of keying features and by means of a second pair of keying features. The second pair of keying features comprises a second keying feature 364 on the second engaging section 362 of the limiter 360 and a second keying feature 44 on or intersecting the second keying structure 42 of the dose tracking member 40.

Moreover, from FIGS. 32 and 33 it is apparent that there are provided at least two radially inwardly extending tappets 380 or pins along an inside facing sidewall portion of the proximal end 369 of the limiter 360. By means of several and circumferentially distributed tappets 380 a rather smooth and purely axial displacement of the limiter 360 free of tilt or cant can be provided.

With the example according to FIGS. 23 through 33 it is of particular benefit, that axial load applied to the trigger 50 is substantially entirely counteracted by the blocking elements 370, 372 if the injection device 1 is in a blocking configuration as shown in FIG. 24. Axial load applied to the trigger 50 in distal direction is transferred via the blocking elements 370, 372 towards and into the handle 90. Since the handle 90 is axially supported by the housing 10 the axial load path in the blocking configuration is located outside the mechanical interaction of the limiter 360 and the dose tracking member 40. Axial load acting on the trigger 50 in the locking configuration is directly transferred via the blocking elements 370, 372 into the handle 90 and into the housing 10. The mechanical components of the dose setting mechanism 3 and the mechanical components of the windup expelling mechanism 2 and their mechanical engagement or interaction does not have to withstand axial load applied to the trigger 50 when the injection device 1 is in the locking configuration. This is beneficial for a long-lasting and reliable operational capability of the windup expelling mechanism 2 and the dose setting mechanism 3.

In the following some further components of the dose setting mechanism 3 and of the windup expelling mechanism 2 are described exemplary with regards to the example of an injection device 1 as shown in FIGS. 1 and 2. This example is only illustrative of one injection device of a plurality of injection devices to which the concept of the dose tracking member 40 and the limiter 60 as described herein is generally applicable.

The windup expelling mechanism 2 comprises the piston rod 30. The piston rod 30 comprises a pressure piece or a bearing 31 at its distal end. The bearing 31 is rotatably supported on a distal tip of the piston rod 30. The bearing 31 is configured to axially abut against a proximally facing end face of the bung 22 of the cartridge 20. The piston rod 30 comprises an outer thread 32 that is threadedly engaged with correspondingly shaped threaded nut 33 which is permanently fixed to the main housing component 14.

The threaded nut 33 comprises a threaded through opening through which the piston rod 30 extends. A rotation of the piston rod 30 relative to the threaded nut 33 in a dose decrementing direction leads to a distally directed advancing motion of the piston rod 30 during a dose dispensing procedure.

The piston rod 30 further comprises at least one or two axially extending grooves on its outer circumference intersecting the outer thread 32. The grooves are in permanent keyed engagement with correspondingly shaped radially inwardly extending protrusions of a spline nut 34. The spline nut 34 comprises radially outwardly extending and radially deflectable clicker arms that bump over correspondingly-shaped teeth on the inside surface of the main housing component 14, thereby creating an audible dispensing click during dose dispensing.

The piston rod 30 axially extends through the hollow drive sleeve 25. The drive sleeve 25 is selectively rotationally engageable with the handle 90. The handle 90 is axially fixed to the main housing component 14. It is rotatable relative to the main housing component 14. The handle 90 comprises a dose dial to set or to select a dose of variable size.

The drive sleeve 25 is snapped to a ratchet sleeve 80 that is radially sandwiched between the dose tracking member 40 and the drive sleeve 25. The drive sleeve 25 and the ratchet sleeve 80 are axially fixed. The drive sleeve 25 is rotatable relative to the ratchet sleeve 80 within a limited range so as to provide a small amount of rotational play.

The mechanical energy reservoir 75 in the form of a helically wound spring is radially sandwiched between the drive sleeve 25 and the ratchet sleeve 80. One axial end 76 of the mechanical energy reservoir 75 is connected to an insert 95 axially and rotationally fixed to the proximal end of the main housing component 14. The other axial end 77 of the mechanical energy reservoir 75 is connected to the ratchet sleeve 80. The insert 95 also serves as a zero-dose stop. It provides an abutment for the dose tracking member 40 when the dose tracking member 40 reaches the zero-dose configuration, typically at the end of a dose dispensing procedure.

The dose tracking member 40 provides and serves as a number sleeve 70. It comprises an outer threaded section 41, 42 threadedly engaged with an inner threaded section 11 of the main housing component 14. In addition the dose tracking member 40 is in permanent splined engagement with the ratchet sleeve 80. The splined engagement of the ratchet sleeve 80 and the dose tracking member 40 comprises an elongated groove provided on one of the dose tracking member 40 and the ratchet sleeve 80 and a correspondingly shaped protrusion or pin located on the other one of the dose tracking member 40 and the ratchet sleeve 80. In this way the dose tracking member 40 is permanently rotationally fixed to the ratchet sleeve 80. At the same time and due to the threaded engagement with the main housing component 14 the dose tracking member 40 is subject to a helical motion during dose setting and during dose dispensing so as to provide a sequence of decreasing or increasing numbers in the dosage window 17.

Between the ratchet sleeve 80 and the spline nut 34 there is provided a locking nut 36. The locking nut 36 is rotationally locked to the main housing component 14 by means of external ribs engaging with correspondingly shaped teeth in the main housing component 14. As indicated in FIG. 1 a ratchet arm of the ratchet sleeve 80 clicks over ratchet teeth inside the locking nut 36. In this way, the ratchet sleeve 80 is rotatable in a dose incrementing or dose decrementing direction in discrete steps. The ratchet arm of the ratchet sleeve 80 is strong enough to prevent stored energy of the mechanical energy reservoir 75 to dissipate in an uncontrolled way. The ratchet arm prevents the helical spring from unwinding.

On the outer circumference and near the proximal end of the drive sleeve 25 there are provided clutch teeth to engage with correspondingly-shaped clutch teeth of the handle 90. In this way and when in the idle position i as shown in FIG. 2 the handle 90 is rotationally engaged with the drive sleeve 25. A rotation of the handle 90 equally translates into a respective rotation of the drive sleeve 25. Since the drive sleeve 25 is rotationally engaged with the ratchet sleeve 80 also the ratchet sleeve 80 is subject to a respective rotation. The rotation of the handle 90 in a dose incrementing direction drives the drive sleeve 26 and hence the ratchet sleeve 80 in the same direction. Since the ratchet sleeve 80 is connected to one end 77 of the mechanical energy reservoir 75 a rotation of the ratchet sleeve 80 further arms or biases mechanical energy reservoir 75.

The mechanical energy stored in the mechanical energy reservoir 75 is constrained and stored in the windup expelling mechanism 2 because the ratchet arm of the ratchet sleeve 80 is prevented from rotating in the opposite direction through its engagement with teeth provided on the inside of the locking nut 36.

There is further provided a last dose nut having external ribs that engage grooves inside the drive sleeve 25. As the handle 90 is rotated the drive sleeve 25 rotates the last dose nut which climbs up outer thread 32 of the piston rod 30. When the residual amount of medicament left in the cartridge is less than a dose intended to be set and when hence a last dose is selected the last dose nut engages stop features at the proximal end of the piston rod 30. Then a further rotation of the handle 90 in a dose incrementing direction is effectively blocked.

When canceling a dose the drive sleeve 25 is subject to an oppositely directed rotation, hence along a dose decrementing direction. Then and due to the limited rotational play between the drive sleeve 25 and the ratchet sleeve 80 the drive sleeve 25 first rotates relative to the ratchet sleeve 80, thereby compressing a biasing arm. Here, a feature of the drive sleeve slides over the ratchet arm of the ratchet sleeve pushing the ratchet arm inwardly and weakening the ratchet between the ratchet sleeve 80 and the locking nut 36. This allows a user to overcome the ratchet and to decrease a dose during a dose setting procedure.

For dispensing of a dose the user presses on the trigger 50 in distal direction thereby compressing the trigger spring 51. Accordingly and due to an axial abutment of the bottom of the trigger 50 with a proximal end face 27 of the drive sleeve 25 the drive sleeve 25 is displaced in distal direction. Teeth on the drive sleeve 25 then disengage from clutch teeth in the handle 90. In this way the handle 90 is rotationally disengaged from the drive sleeve 25. Additionally, the locking nut 36 is urged in distal direction together with the drive sleeve 24 and the ratchet sleeve 80, thereby disengaging from the teeth in the housing component 14. Consequently, the locking nut 36 is then free to rotate relative to the housing 10. The mechanical energy reservoir 75 then releases the stored energy and sets the locking nut 36 in rotation. The locking nut 36 is rotationally coupled to the spline nut 34. Therefore, the spline nut 34 is rotated in a dose decrementing direction by the locking nut 36. Due to the keyed engagement of the spline nut 34 with the piston rod 30 the piston rod 30 starts to rotate. Due to the threaded engagement of the piston rod 30 with the threaded not 33 that is fixed inside the housing component 14 the piston rod 30 is subject to a combined rotational and longitudinal motion towards the distal end 5 of the injection device 1.

Since the dose tracking member 40 is permanently in keyed engagement with the ratchet sleeve 80 numbers printed on the display portion 45 of the dose tracking member 70 are displayed in the dosage window 17 as a dose is dialed. During the dose dispensing procedure the numbers in the dosage window 17 are displayedin a decreasing order.

Releasing of the trigger 50 prior to reach a zero-dose configuration re-engages the locking nut 36 to the housing component 14 and the dispensing procedure will be immediately stopped until the trigger 50 is pressed again.

LIST OF REFERENCE NUMBERS 1 injection device
2 expelling mechanism
3 dose setting mechanism
4 proximal end
5 Distal end
6 medicament
10 housing
11 threaded section
12 slotted link
13 cartridge holder
14 main housing component
15 outer thread
16 engaging section
17 dosage window
20 cartridge
21 barrel
22 bung
23 pierceable seal
24a engaging section
24b engaging section
25 drive sleeve
26 flange
27 end face
28 protrusion
29 spline feature
30 piston rod
31 bearing
32 outer thread
33 threaded nut
34 spline nut
36 locking not
40 dose tracking member
41 keying structure
42 keying structure
43 keying feature
44 keying feature
45 display portion
49 end section
50 trigger
51 trigger spring
52 strut portion
53 button portion
54 end face
55 radial protrusion
56 radial protrusion
60 limiter
61 engaging section
62 engaging section
63 keying feature
64 keying feature
65 leg
66 leg 67 proximal end face
68 protrusion
69 proximal end section
70 number sleeve
75 mechanical energy reservoir
76 axial end
77 axial end
80 ratchet sleeve
90 handle
91 inner sleeve
92 connecting link
95 insert
140 dose tracking member
141 keying structure
142 keying structure
143 keying feature
144 keying feature
145 tracking sleeve
146 engaging section
160 limiter
161 engaging section
162 engaging section
163 keying feature
164 keying feature
165 leg
166 leg
167 border
168 through opening
169 proximal end section
170 number sleeve
171 threaded section
172 display portion
173 keying structure
210 interface member
211 spline feature
212 through opening
214 splined feature
240 dose tracking member
241 keying structure
242 keying structure
243 keying feature
244 keying feature
245 display portion
250 trigger
251 button
252 proximal end face
253 sidewall
254 distal end section
255 stem
256 flange section
257 counterpart section
258 splined feature
260 limiter
261 engaging section
262 engaging section
263 keying feature
264 keying feature
265 leg
266 leg
267 beveled section
268 radial gap
360 limiter
361 engaging section
362 engaging section
363 keying feature
364 keying feature
365 leg 366 leg
367 beveled edge
368 beveled section
369 proximal end
370 blocking element
371 proximal end
372 blocking element
373 proximal end
374 distal end
375 distal end
376 through opening
380 tappet

The invention claimed is:

1. An injection device for expelling of a number of preset or user-selectable doses of a medicament, the injection device comprising:
an elongated housing extending along an axial direction and configured to accommodate a cartridge, the cartridge containing the medicament and having a bung sealing a proximal end of the cartridge;
a windup expelling mechanism comprising a piston rod, a mechanical energy reservoir, and a trigger, wherein the trigger is movable between an idle position and a dose expelling position relative to the housing and configured to, when moved into the dose expelling position, release energy from the mechanical energy reservoir to axially drive the piston rod relative to the housing in order to drive the bung; and
a dose setting mechanism comprising
a handle for rotationally selecting a dose of the medicament and/or for arming the windup expelling mechanism,
a dose tracking member rotatable relative to the housing within a range of positional states during selecting of the dose, the dose tracking member being operatively connectable to the handle for tracking a rotation of the handle, and
a limiter movable relative to the dose tracking member, wherein the limiter is operationally engageable with the dose tracking member and the trigger for blocking actuation of the trigger when the dose tracking member is in one of a number of predetermined sections of the range of positional states.

2. The injection device according to claim 1, wherein operational engagement between the dose tracking member and the limiter comprises a first pair of keying features and a second pair of keying features that are located on the limiter and on the dose tracking member.

3. The injection device according to claim 2, wherein the dose tracking member is engaged with the housing by a slotted link arranged along a cylindrical surface, and wherein movement of the dose tracking member includes a rotation around a longitudinal axis of the cylindrical surface.

4. The injection device according to claim 3, wherein the operational engagement between the dose tracking member and the limiter comprises one or more elongated keying structures, wherein each of the one or more elongated keying structures are arranged in parallel or are formed integrally with the slotted link between the dose tracking member and the housing.

5. The injection device according to claim 4, wherein the one or more elongated keying structures comprise at least one of a first outer thread and a second outer thread on an outside surface of the dose tracking member.

6. The injection device according to claim 5, wherein the slotted link comprises an inner threaded section on the housing and comprises at least one of the first outer thread or the second outer thread on the dose tracking member.

7. The injection device according to claim 1, wherein the handle is operatively connectable to the mechanical energy reservoir for harvesting energy from rotational actuation of the handle and for arming the mechanical energy reservoir.

8. The injection device according to claim 1, wherein the limiter is axially connected to the trigger for transferring axial-translational forces from the limiter to the trigger.

9. The injection device according to claim 1, wherein the trigger is axially displaceable relative to the housing, wherein the limiter is axially engageable with the trigger and wherein the limiter has a first engaging section and a second engaging section wherein the first engaging section is circumferentially offset from the second engaging section.

10. The injection device according to claim 9, wherein:
operational engagement between the dose tracking member and the limiter comprises a first pair of keying features and a second pair of keying features that are located on the limiter and on the dose tracking member, and
at least one of the first pair of keying features or the second pair of keying features comprise a radially inwardly extending protrusion to engage with at least one of a first outer thread or a second outer thread on an outside surface of the dose tracking member.

11. The injection device according to claim 10, wherein at least one of the first outer thread or the second outer thread is discontinuous and comprises a first recess, wherein the first recess is shaped to receive the radially inwardly extending protrusion.

12. The injection device according to claim 10, wherein at least one of the first outer thread or the second outer thread is discontinuous and comprises a first recess, wherein the protrusion is axially displaceable through the first recess.

13. The injection device according to claim 1, wherein the limiter comprises a proximal end section to engage with the trigger and wherein the limiter is axially displaceable relative to the housing between a proximal blocking position and a distal release position.

14. The injection device according to claim 1, wherein the mechanical energy reservoir comprises a helical driving spring having a first end connected to the housing and having a second end connected to the dose tracking member and wherein the dose tracking member is rotatable in a dose incrementing direction against an action of the driving spring.

15. The injection device according to claim 1, further comprising a driver axially displaceable between a dose setting position and a dose dispensing position and wherein the handle is rotatable relative to the housing for setting of a dose of the medicament, wherein when in the dose dispensing position the driver is rotationally locked to the piston rod and is rotationally disengaged from the handle and wherein when in the dose setting position, the driver is rotationally disengaged from the piston rod and is rotationally locked to the handle.

16. The injection device according to claim 1, further comprising a cartridge filled with the medicament and arranged inside the housing.

17. An injection device for expelling of a number of preset or user-selectable doses of a medicament, the injection device comprising:
a housing configured to accommodate a cartridge containing the medicament;
an expelling mechanism comprising a piston rod and a trigger, the trigger movable between an idle position and a dose expelling position relative to the housing to release energy from the expelling mechanism to axially drive the piston rod to expel medicament from the cartridge; and
a dose setting mechanism comprising
a handle for rotationally selecting a dose of the medicament and/or for arming the expelling mechanism,
a dose tracking member rotatable relative to the housing within a range of positional states during selecting of the dose, the dose tracking member being operatively connectable to the handle for tracking a rotation of the handle, and
a limiter movable relative to the dose tracking member, wherein the limiter is operationally engageable with the dose tracking member and the expelling mechanism for blocking actuation of the expelling mechanism when the dose tracking member is in one of a number of predetermined sections of the range of positional states, the limiter being axially connected to the trigger for transferring axial-translational forces from the limiter to the trigger.

18. The injection device according to claim 17, wherein operational engagement between the dose tracking member and the limiter comprises a first pair of keying features and a second pair of keying features that are located on the limiter and on the dose tracking member.

19. The injection device according to claim 18, wherein the dose tracking member is engaged with the housing by a slotted link arranged along a cylindrical surface, and wherein movement of the dose tracking member includes a rotation around a longitudinal axis of the cylindrical surface.

20. An injection device for expelling of a number of preset or user-selectable doses of a medicament, the injection device comprising:
a housing configured to accommodate a cartridge containing the medicament;
an expelling mechanism comprising a piston rod and a trigger, the trigger movable between an idle position and a dose expelling position relative to the housing to release energy from the expelling mechanism to axially drive the piston rod to expel medicament from the cartridge; and
a dose setting mechanism comprising
a handle for rotationally selecting a dose of the medicament and/or for arming the expelling mechanism,
a dose tracking member rotatable relative to the housing within a range of positional states during selecting of the dose, the dose tracking member being operatively connectable to the handle for tracking a rotation of the handle, and
a limiter movable relative to the dose tracking member, wherein the limiter is operationally engageable with the dose tracking member and the expelling mechanism for blocking actuation of the expelling mechanism when the dose tracking member is in one of a number of predetermined sections of the range of positional states, wherein the limiter comprises a proximal end section to engage with the trigger and is axially displaceable relative to the housing between a proximal blocking position and a distal release position.

* * * * *